US010244765B2

(12) United States Patent
Pierce et al.

(10) Patent No.: US 10,244,765 B2

(45) Date of Patent: Apr. 2, 2019

(54) INHIBITING OR REDUCING FUNGAL GROWTH

(71) Applicant: GEORGIA STATE UNIVERSITY RESEARCH FOUNDATION, INC., Atlanta, GA (US)

(72) Inventors: George E. Pierce, Canton, GA (US); Sidney Crow, Smyrna, GA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 0 days.

(21) Appl. No.: 15/984,795

(22) Filed: May 21, 2018

(65) Prior Publication Data

US 2018/0332859 A1 Nov. 22, 2018

Related U.S. Application Data

(62) Division of application No. 14/773,867, filed as application No. PCT/US2014/026371 on Mar. 13, 2014, now Pat. No. 10,004,237.

(60) Provisional application No. 61/783,395, filed on Mar. 14, 2013, provisional application No. 61/783,573, filed on Mar. 14, 2013.

(51) Int. Cl.

| | |
|---|---|
| ***C12N 9/00*** | (2006.01) |
| ***A01N 63/02*** | (2006.01) |
| ***C12N 1/20*** | (2006.01) |
| ***A01N 63/00*** | (2006.01) |

(52) U.S. Cl.

CPC ............. *A01N 63/02* (2013.01); *A01N 63/00* (2013.01); *C12N 1/20* (2013.01); *C12Y 305/05* (2013.01); *C12Y 401/99* (2013.01); *C12Y 402/01084* (2013.01); *C12Y 404/01009* (2013.01)

(58) Field of Classification Search

CPC . C12N 1/20; C12N 9/00; A01N 63/00; A01N 63/02; C12Y 305/05; C12Y 401/99

See application file for complete search history.

(56) References Cited

U.S. PATENT DOCUMENTS

| | | | |
|---|---|---|---|
| 3,940,316 | A | 2/1976 | Commeyras et al. |
| 4,001,081 | A | 1/1977 | Commeyras et al. |
| 4,343,900 | A | 8/1982 | Watanabe |
| 4,880,739 | A | 11/1989 | Yamada et al. |
| 5,089,411 | A | 2/1992 | Yamada et al. |
| 5,260,302 | A | 11/1993 | Fattori et al. |
| 5,409,509 | A | 4/1995 | Burth et al. |
| 5,512,466 | A | 4/1996 | Klee et al. |
| 5,545,815 | A | 8/1996 | Fischer et al. |
| 5,664,368 | A | 9/1997 | Sandor |
| 5,807,730 | A | 9/1998 | Ito et al. |
| 5,863,750 | A | 1/1999 | Pierce |
| 6,060,265 | A | 5/2000 | Pierce |
| 6,132,985 | A | 10/2000 | Pierce |
| 6,133,001 | A | 10/2000 | Homann et al. |
| 6,133,196 | A | 10/2000 | Ocamb et al. |
| 6,133,421 | A | 10/2000 | Fallon et al. |
| 6,153,415 | A | 11/2000 | Oriel et al. |
| 6,156,956 | A | 12/2000 | Theoglis et al. |
| 6,194,193 | B1 | 2/2001 | Drahos et al. |
| 6,214,603 | B1 | 4/2001 | Oriel et al. |
| 6,228,633 | B1 | 5/2001 | Oriel et al. |
| 6,242,242 | B1 | 6/2001 | Oriel et al. |
| 6,251,388 | B1 | 6/2001 | Durden |
| 6,287,828 | B1 | 9/2001 | Oriel et al. |
| 6,316,242 | B1 | 11/2001 | Endo et al. |
| 6,426,105 | B1 | 7/2002 | Palta et al. |
| 6,524,998 | B1 | 2/2003 | Kloepper et al. |
| 6,606,822 | B2 | 8/2003 | Bonfiglio |
| 6,613,435 | B1 | 9/2003 | Guritza |
| 6,649,397 | B1 | 11/2003 | Nakamura |
| 6,677,149 | B2 | 1/2004 | Dicosimo et al. |
| 6,730,508 | B1 | 5/2004 | Ito et al. |
| 6,735,902 | B1 | 5/2004 | Ahm |
| 6,955,911 | B2 | 10/2005 | Ryuno et al. |
| 6,995,007 | B2 | 2/2006 | Gunner et al. |
| 7,084,321 | B2 | 8/2006 | Pais et al. |
| 7,213,366 | B1 | 5/2007 | Ahm |
| 7,244,595 | B2 | 7/2007 | Uehara et al. |
| 7,405,064 | B2 | 7/2008 | Payne et al. |
| 7,504,557 | B2 | 3/2009 | Gallie et al. |
| 7,531,343 | B2 | 5/2009 | Pierce et al. |
| 7,531,344 | B2 | 5/2009 | Pierce et al. |
| 2001/0019728 | A1 | 9/2001 | Basinger et al. |

(Continued)

FOREIGN PATENT DOCUMENTS

| | | |
|---|---|---|
| CN | 1384709 | 12/2002 |
| CN | 1547609 | 11/2004 |

(Continued)

OTHER PUBLICATIONS

Alexander and Grierson, "Ethylene biosynthesis and action in tomato: a model for climacteric fruit ripening" J. Exp. Botany, 53:2039-55 (2002).

(Continued)

*Primary Examiner* — Ruth A Davis

(74) *Attorney, Agent, or Firm* — Thomas|Horstemeyer, LLP

(57) ABSTRACT

Provided are methods and compositions for inhibiting or reducing fungal growth. The methods comprise exposing a location to a composition comprising one or more enzymes, one or more bacteria, and/or an enzymatic extract, wherein the one or more enzymes, one or more bacteria, and/or the enzymatic extract isolated from one or more bacteria are exposed to location in a quantity sufficient to inhibit or reduce fungal growth.

30 Claims, 17 Drawing Sheets

(56) References Cited

U.S. PATENT DOCUMENTS

| | | | |
|---|---|---|---|
| 2002/0139046 | A1 | 10/2002 | Weber et al. |
| 2003/0044807 | A1 | 3/2003 | Bramucci et al. |
| 2003/0049807 | A1 | 3/2003 | Salvo et al. |
| 2003/0084609 | A1 | 5/2003 | Perriello et al. |
| 2003/0093946 | A1 | 5/2003 | Gutierrez Pavez |
| 2003/0115633 | A1 | 6/2003 | Pais et al. |
| 2004/0072694 | A1 | 4/2004 | Perriello et al. |
| 2004/0106165 | A1 | 6/2004 | Reisinger et al. |
| 2005/0014243 | A1 | 1/2005 | Uehara et al. |
| 2005/0066389 | A1 | 3/2005 | Gallie et al. |
| 2005/0227356 | A1 | 10/2005 | Lessard et al. |
| 2006/0259993 | A1 | 11/2006 | Barton et al. |
| 2007/0068072 | A1 | 3/2007 | Xavier et al. |
| 2007/0090122 | A1 | 4/2007 | Zeypang |
| 2007/0184528 | A1 | 8/2007 | Pierce |
| 2007/0184543 | A1 | 8/2007 | Pierce |
| 2007/0259783 | A1 | 11/2007 | Tateishi et al. |
| 2008/0236038 | A1 | 10/2008 | Pierce et al. |
| 2012/0122684 | A1 | 5/2012 | Bais et al. |
| 2013/0035232 | A1 | 2/2013 | Pierce et al. |

FOREIGN PATENT DOCUMENTS

| | | |
|---|---|---|
| EP | 0109083 | 5/1984 |
| EP | 0243966 | 11/1987 |
| EP | 0243967 | 11/1987 |
| EP | 0307926 | 3/1989 |
| EP | 0353689 | 2/1990 |
| EP | 0362829 | 4/1990 |
| EP | 0790310 | 8/1997 |
| JP | 2010136668 | 6/2010 |
| PL | 161863 | 8/1993 |
| RU | 829484 | 5/1981 |
| WO | WO95020040 | 7/1995 |
| WO | WO9528085 | 10/1995 |
| WO | WO1998027016 | 6/1998 |
| WO | WO1992012249 | 8/1999 |
| WO | WO1999040177 | 8/1999 |
| WO | WO0013505 | 3/2000 |
| WO | WO2000044230 | 8/2000 |
| WO | WO2000051435 | 9/2000 |
| WO | WO2000036085 | 8/2002 |
| WO | WO2002072856 | 9/2002 |
| WO | WO2003037066 | 5/2003 |
| WO | WO2006032530 | 3/2006 |
| WO | WO2007090122 | 8/2007 |
| WO | WO2008124307 | 4/2009 |
| WO | WO2011091374 | 7/2011 |
| WO | WO2012067668 | 5/2012 |
| WO | WO2013007398 | 1/2013 |
| WO | WO2013019604 | 2/2013 |

OTHER PUBLICATIONS

Avni et al., "Induction of ethylene biosynthesis in Nicotiana tabacum by a Trichoderma viride sylanase is correlated to the accumulation of 1-aminocyclopropane-1-carboxylic acid (ACC) synthase and ACC oxidase transcripts" Plant Physiol. 106:1049-55 (1994).

Badr et al., "Kinetics and properties of L-glutaminase and L-asparaginase activities of Pseudomonas ovalis," Badt. II. Abt. 131:489-96 (1976).

Bahr and Bonner, Jr., "Cyanide-insensitive respiration" J. Biol. Chem. 248: 3446-50 (1973).

Bates and Warner, "1-MCP and Fruit Quality," Perishables Handling Quarterly, Issue No. 108, (Nov. 2001) postharvest.ucdavis.edu/datastorefiles/234-37.pdf.

Beaudoin et al., "Interactions between abscisic acid and ethylene signaling cascades," The Plant Cell 12:1103-15 (2000).

Bijnen et al., "Geometrical optimization of a longitudinal resonant photoacoustic cell for sensitive and fast trace gas detection" Rev. Sci. Instrum. 67: 2914-23 (1996).

Blankenship and Dole, "1-Methylcyclopropene: a review." Postharvest Biol. Technol. 28:1-25 (2003).

Bleecker and Kende, "Ethylene: a gaseous signal molecule in plants." Ann. Rev. Cell. Dev. Biol. 16:1-18 (2000).

Bowyer and Wills, "Delaying postharvest senescence of cut flowers using nitric oxide," Rural Industries Research and Development Corporation, (May 2003). www.rirdc.gov.au/reports/WNP/03-015.pdf.

Bucke, C., "Cell Immobilization in Calcium Alginate," Methods in Enzymology, vol. 135, 1987, pp. 175-189.

Bunch et al., "Biotransformation of nitriles by Rhodococci" Antonie van Leeuwenhoek, Kluwer Academic Publishers, The Netherlands 74:89-97 (1998).

Cai et al., Study on Immobilization of the Cell of Niteile Hydratase by Flocculation, Chemical Technology Market, 3:39-42 (2005).

Chamani et al., "Ethylene and anti-ethylene treatment effects on cut 'First Red' rose," Journal of Applied Horticulture, 7(1): 3-7 (2005).

"Chiquita explores financial alternatives," Refrigerated Transporter, Sep. 29, 2006, http://refrigeratedtrans.com/marr/transpoation_chiquita_explores_financial/index.html.

Colby et al., Immobilization of Rhodococcus AJ270 and Use of Entrapped Biocatalyst for the Production of Acrylic Acid, Monatshefte für Chemice, 131:655-666 (2000).

Collins, et al., "The Utilization of Nitriles and Amides by Nocardia rhodochrous," J. Gen Microbiol., vol. 129, 1983, pp. 711-718.

Crassweller, Pennsylvania State University, Horticulture 432, Lecture Notes. Thinning and PGRs, (2000). www.hortweb.cas.psu.edu/courses/hort432/lecturenotes/pgr.html.

Crisoto, "Stone fruit maturity indices: a descriptive review," Postharvest News and Information 5(6):65N-68N (1994).

Cristescu et al., "Ethylene production by Botrytis cinerea in vitro and in tomatoes." Appl. Environ. Microbial. 68:5342-50 (2002).

Curry and Thompson, "Delicious quality can be affected by ethephon or ReTain," Washington University—Tree Fruit Research and Extension Center: Postharvest Information Network, 15th Annual Postharvest Conference, Mar. 9-10, 1999. http://postharvest.tfrec.wsu.edu/pgDisplay.php?article=PC99A.

Difco Manual of Dehydrated Culture Media and Reagents for Microbiological and Clinical Laboratory Procedures, 9th Ed., 1953, pp. 264-265.

Dixon and Palva, "Stress-induced phenylpropanoid metabolism." Plant Cell. 7:1085-97 (1995).

Dominguez et al., "Effect of inhibitors of ethylene biosynthesis and action on ripening of bananas." Proc. Int. Symp. Bananas in Subtropics (V. Galan Sauco, Editor) 519-28 (1998).

Dong et al., "Purification and characterization of 1-aminocyclopropane-1-carboxylate oxidase from apple fruit," Proc. Natl. Acad. Sci. USA, 89:9789-93 (1992).

El-Sharkawy et al., "Isolation and characterization of four ethylene perception elements and their expression during ripening in perars (*Pyrus communis* L.) with/without cold requirement." J Exp. Botany. 54:1615-25 (2003).

Fawcett et al., "A Rapid and Precise Method for the Determination of Urea", J. Clin. Path. 13:156-9 (1960).

Ferreira, J., et al., "Comparison of three different methods for trehalose determination in yeast extracts," Food Chemistry, vol. 60, No. 2, pp. 251-254.

Foda et al., "Formation and properties of L-glutaminase and L-asparaginase activities in Pichia polymorpha," Acta Microbiol. Pol. 29(4):343-52 (1980).

Fisher et al., "Bacillus subtilis 168 contains two differentially regulated genes encoding L-asparaginase" J. Bacteriol. 184(8):2148-54 (2002).

Frankenberger WT and Tabatabai MA. Amidase and urease activities in plants. Plant and Soil 1982, 64(2):153-166.

Fournand et al., "Acyl transfer activity of an amidase from *Rhodococcus* sp. Strain R312: Formation of a wide range of hydroxamic acids" Applied and Environmental Microbiology 64(8):2844-52 (1998).

Goda et al., "Discovery of a novel enzyme, isonitrile hydratase, involved in nitrogen-carbon triple bond cleavage" J. Biol. Chem. 276(26):23480-5 (2001).

Hann et al., "5-Cyanovaleramide Production Using Immobilized Pseudomonas Chlororaphis B23", Bioorg. Medicinal Chem., 7:2239-45 (1999).

(56) References Cited

OTHER PUBLICATIONS

Harper, D., "Characterization of a Nitrilase from *Nocardia* sp. (Rhodochrous Group) N.C.I.B. 11215, Using p-Hydroxybenzonitrile as Sole Carbon Source," Int. J. Biochem, vol. 17, No. 6, 1985, pp. 677-683.

Harper, D., "Microbial metabolism of aromatic nitriles," Enzymology of C—N cleavage by *Nocardia* sp. (Rhodochrous group) N.C.I.B. 11216, Biochem J., vol. 165, No. 2, 1977, pp. 309-319.

Huber et al., "Use of 1-methylcyclopropene (1-MCP) on tomato and avocado fruits: potential for enhanced shelf life and quality retention," University of Florida, IFAS Extension, (2003). http://edis.ifas.ufl.edu/HS151.

Itai et al., "Rapid identification of 1-minocyclopropane-1-carboxylate (ACC) synthase genotypes in cultivars of Japanese pear (*Pyruspyrifolia nakai*) using CAPS markers." Theor. Appl. Genet. 106:1266-72 (2003).

Johnson and Ecker, "The ethylene gas signal transduction pathway: a molecular perspective." Ann. Rev. Genetics. 32: 227-54 (1998).

Jun, C., "Study on Immobilization of the Cells of Niteile Hydratase by Flocculation," Chemical Technology Market, vol. 3, 2005, pp. 39-42.

Kader, "A summary of CA requirements and recommendations for fruits other than apples and pears," Postharvest Horticulture Series No. 22A, University of California, Davis, pp. 29-70 (2001).

Kader et al., "Postharvest handling and physiology of horticultural crops: a list of selected references," University of California Postharvest Group (May 2001).

Kato et al., "Nitrile hydratase involved in aldoxime metabolism from *Rhodococcus* sp. strain YH3-3 purification and characterization" Eur. J. Biochem. 263(3):662-70 (1999).

Kerr, JR., Bacterial inhibition of fungal growth and pathogenicity; Microbial Ecology in Health and Disease 1999, vol. 11, No. 3, pp. 129-142.

Klee et al., "Control of ethylene synthesis by expression of a bacterial enzyme in transgenic tomato plants." Plant Cell. 3:1187-93 (1991).

Kobayashi, M., et al., "Versatile nitrilases: Nitrile-hydrolysing enzymes," FEMS Microbiology, vol. 120, 1994, pp. 217-224.

Kobayashi, M., et al., "Metalloenzyme nitrile hydratase: Structure, regulation and application to biotechnology," Nature Biotechnology, vol. 16, 1998, pp. 733-736.

Komeda et al., "Characterization of the gene cluster of high-molecular-mass nitrile hydratase (H-NHase) induced by its reaction produce in Rhodococcus rhodochrous J1" Proc. Natl. Acad. Sci. USA 93:4267-72 (1996).

Kopf et al., "Key Role of Alkanoic Acids on the Spectral Properties, Activity, and Active-Site Stability of Iron-Containing Nitrile Hydratase From Brevibacterium R312" Eur J. Biochem. 240:239-44 (1996).

Kozdroj et al., "Influence of introduced potential biocontrol agents on maize seedling gorwth and bacterial community structure in the rhizosphere" Soil Biol. Biochem. 36(11):1775-84 (2004).

Kulayeva, Ethylene in the life of plants, Soros Educational J., 11:78-84 (1998).

Kulikova et al., "Ethylene epoxidation by native and immobilized cells of the propane-assimilating culture Rhodococcus erythropolis 3/89," Prikladnaya Biokhima I Mikrobiologiya 35(6):611-15 (1999).

Lafuente et al., "Phenylalanine ammonia-lyase as related to ethylene in the development of chilling symptoms during cold storage of citrus fruit." J. Agric. Food Chem. 49:6020-5 (2001).

Lawton et al., "Regulation of senescence-related gene expression in carnation flower petals by ethylene," Plant Physiol. 93:1370-5 (1990).

Liao et al., "Postharvest life of cut rose flowers as affected by silver thiosulfate and sucrose," Bot. Bull. Acad. Sin. 41:299-303 (2000).

Linton, E., et al., "Utilization of Aliphatic Amides and Nitriles by Nocardia rhodochrous LL100-21," Journal of General Microbiology, vol. 132, 1986, pp. 1493-1501.

López-Gallego, F., et al., "Enzyme stabilization by glutaraldehyde crosslinking of adsorbed proteins on aminated supports," Journal of Biotechnology, vol. 119, 2005, pp. 70-75.

Mafra et al., Ripening-related changes in the cell walls of olive (*Olea europea* L.) pulp of two consecutive harvests, J. Sci. Food Agric. 86:988-98 (2006).

Marcos et al., "Involvement of ethylene biosynthesis and perception in the susceptibility of citrus fruits to Penicillium digitatum infection and the accumulation of defence-related mRNAs." J. Exp. Botany. 56: 2183-93 (2005).

Martinkova, et al., "Nitrile- and amide-converting microbial enzymes: stereo-, regio-chemoselecivity" Biocatalysis and Biotransformation 20(2):73-93 (2002).

Mascharak, PK. Structural and functional models of nitrile hydratase. Coordination Chemistry Reviews 2002, 225(1):201-214.

Mathooko, "Regulation of ethylene biosynthesis in higher plants by carbon dioxide," Postharvest Biology and Technology 7:1-26 (1996).

Mayak and Dilley, "Regulation of senescence in carnation (*Dianthus caryophyllus*): effect of absiscic acid and carbon dioxide on ethylene production," Plant Physiol. 58:663-5 (1972).

Mayak and Halevy, "Interrelationships of ethylene and abscisic acid in the control of rose petal senescence," Plant Physiol. 50:341-6 (1972).

McDaniel, Virginia Polytechnic University, Horticulture 2164 Lecture Notes, R-8, (1999). http://www.hort.vt.edu/faculty/McDaniel/hort2164/R&DistributionandHandling.htm.

Merritt et al., "Inhibitors of ethylene synthesis inhibit auxin-induce stomatal opening in epidermis detached from leaves of *Vicia faba* L." Plant Cell Physiol 42:223-30 (2001).

Mullins, University of Florida, BOT 6566 (Plant Growth and Development), Lecture Notes 12: Seed and Fruit Development (2000).

Nagasawa et al., "Optimum Culture Conditions for the Production of Benzonitrilase by Rhodococcus Rhodochrous J1" Arch. Microbiol. 150:89-94 (1988).

Nagasawa et al., "Occurrence of a Cobalt-Induced and Cobalt-Containing Nitrile Hydratase in Rhodococcus Rhodochrous J1" Biochem. Biophys. Res. Comm. 155:1008-16 (1988).

Nagasawa, et al., "Optimum culture conditions for the production of cobalt-containing nitrile hydratase by Rhodococcus rhodochrous J1" Applied Microbiology and Biotechnology 34:783-8 (1991).

Nagasawa et al., "Characterization of a new cobalt-containing nitrile hydratase purified from urea-induced cells of Rhodococcus rhodochrous J1," Eur. J. Biochem. 196:581-9 (1991).

Nagasawa et al., "Nitrilase of Rhodococcus rhodochrous J1. Conversion into the active form by subunit association" Eur. J. Biochem. 267(1):138-44 (2000).

Nagasawa, T., et al., "Superiority of Pseudomonas chloroaphis B23 nitrile hydratase as a catalyst for the enzymatic production of acrylamide," Experientia, vol. 45, 1989, pp. 1066-1070.

Nagasawa, T., et al., "The superiority of the third-generation catalyst, Rhodococcus rhodochrous J1 nitrile hydratase, for industrial production of acrylamide," Applied Microbiol. Biotechnol., vol. 40, 1993, pp. 189-195.

Nukui et al., "Repressed ethylene production in the gynoecium of longlasting flowers of the carnation 'White Candle': role of the gynoecium in carnation flower senescence," Journal of Experimental Botany 55 (397): 641-50 (2004).

Pandey et al., "Role of polyamines and ethylene as modulators of plant senescence," J. Biosci. 25(3):291-9 (2000).

Pesis and Faiman, "Inhibition of ethylene production and ACC oxidase activity in avocado by acetaldehyde vapours," Proceedings of the World Avocado Congress 111, 354-361, (1995). www.avocadosource.com/WAC3/WAC3 p354.htm.

Pretel et al., "Ripening and ethylene biosynthesis in controlled atmosphere stored apricots" Eur. Food Res. Technol. 209:130-4 (1999).

Pujade-Renaud et al., "Ehtylene-induced increase in glutamine synthetase activity and mRNA levels in Hevea brasiliensis latex cells" Plant Physiol. 100:131-127 (1994).

Reed et al., "Delayed ripening tomato plants expressing the enzyme 1-aminocyclopropane-1-carboxylic acid deaminase. 1. Molecular characterization, enzyme expression, and fruit ripening traits," J. Agriculture Food 43:1954-62 (1995).

(56) References Cited

OTHER PUBLICATIONS

Rhodes, Purdue University, Horticulture 640—Metabolic Plant Physiology (2008). http://www.hort.purdue.edu/rhodcv/hort640c/sulfate/su00009.htm.
Rychter et al., 1978. "Cyanide-resistant respiration in freshly cut potato slices." Plant Physiol. 61: 667-668.
Sacher, "Permeability characteristics and amino acid incorporation during senescence (ripening) of banana tissue," Plant Physiol. 41:701 -8 (1966).
Saltveit, University of California, Davis. Department of Vegetable Crops. Postharvest Technology Research Information Center [PTRIC] "Respiratory Metabolism" (2006). postharvest.ucdavis.edu.
Sankhian et al., "Nitrile hydratase of Rhodococcus rhodochrous NHB-2: optimization of conditions for production of enzyme and conversion of acrylonitrile to acrylamide" Asian Jr. of Microbiol. Biotech. 5(2):217-33 (2003).
Seong, K-Y., et al., Effect of Trehalose on the Viability of Fluorescent Pseudomonas, Strain SSL3, Korean J. Soil Sci. & Fert., vol. 33, No. 4, 2000, pp. 292-301.
Singh et al., "Effect of cobalt, cadmium, and nickel as inhibitors of ethylene biosynthesis on floral malformation, yield, and fruit quality of mango" J. Plant Nutrition. 17:1659-70 (1994).
Singer, M., et al., "Multiple Effects of Trehalose on Protein Folding In Vitro and In Vivo," Molecular Cell, vol. 1, Apr. 1998, pp. 639-648.
Sisler et al., "Inhibition of ethylene responses by 1-methylcyclopropene and 3-methylcycloproene." Plant Growth Reg. 27:105-11 (1999).
Skjerdal OT, et al. "Changes in intracellular composition in response to hyperosmotic stress of NaCl, sucrose or glutamic acid in Brevibacterium lactofermentum and Corynebacterium glutamicum." Applied Microbiology and Biotechnology. Jan. 1996, vol. 44, Issue 5, pp. 635-642.
SLX International, Inc., User manual and instructions for the SLX International, Inc. model 2024 shipping container (2002). SLX International, Inc. San Luis Obispo, CA.
Solomos and Laties, "Similarities between the actions of ethylene and cyanide in initiating the climacteric ripening of avocados" Plant Physiol. 54:506-11 (1974).
Sonawane et al., "Utilization of acidic amino acids and their amides by Pseudomanads: role of periplasmic glutaminase-asparaginase" Arch. Microbiol. 179:151-9 (2003).
Sonawane et al., "Identification of Pseudomonas proteins coordinately induced by acidic amino acids and their amides: a two-dimensional electrophoresis study" Microbiology 149:2909-18 (2003).
Soong et al., "A novel amidase (half-amidase) for half-amide hydrolysis involved in the bacterial metabolism of cyclic imides" Appl. Environ. Microbiol. 66(5):1947-52 (2000).
Sozzi et al., "Gibberellic acid, synthetic auxins, and ethylene differentially modulate a-I,-arabinofwanosidase activities in antisense 1-aminocyclopropane-1-carboxylic acid synthase tomato pericarp discs," Plant Physiol. 129:1330-40 (2002).
ten Have and Woltering, "Ethylene biosynthetic genes are differentially expressed during carnation (*Dianthus caryophyllus* L.) flower senescence" Plant Molec. Biol. 34:89-97 (1997).
Thompson et al., "Acceleration of membrane senescence in cut carnation flowers by treatment with ethylene," Plant Physiol. 69:859-863 (1982).
Trainotti and Casadoro, "Different ethylene receptors show an increased expdression during the ripening of strawberries: does such an increment imply a role for ethylene in the ripening of these non-climateric fruits," J. Exp. Botany 56:2037-46 (2005).
Tucker TM, et al. "A comparison of mycolic acids profiles of Rhodococcus DAP96253 when grown on different media." Abstracts of the General Meeting of the American Society for Microbiology, vol. 106, 2006, p. 440, & 106th General Meeting of the American-Society-for-Microbiology; Orlando, FL, USA; May 21-25, 2006, available at http://ieg.ou.edu/ASM2006/data/papers/O_100.htm.
Tucker TA, et al. "Effect of growth media on cell envelope composition and nitrile hydratase stability in Rhodococcus rhodochrous strain DAP96253." J Ind Microbiol Biotechnol. Nov. 2012;39(11):1577-85.
Tudela and Primo-Millo, "1-Aminocyclopropane-1-carboxylic acid transported from roots to shoots promotes leaf abscission in Cleopatra Mandarin (Citrus reshni Hort. ex Tan.) seedlings rehydrated after water stress" Plant Physiology 100:131-7 (1992).
U.S. Biological web page capture, http://www.usbio.net/Product.aspx?ProdSku=P3300, Composition of Peptone, Nov. 2007.
Van Doorn, "Does Ethylene Treatment Mimic the Effects of Pollination on Floral Lifespan and Attractiveness?" Annals of Botany 89:375-83 (2002).
Van Doorn, "Effect of Ethylene on Flower Abscission: a Survey" Annals of Botany 89:689-93 (2002).
Van Doorn, "Categories of petal senescence and abscission: a re-evaluation" Annals of Botany 87:447-56 (2001).
Wagstaff et al., "Ethylene and flower longevity in Alstroemeria: relationship between tepal senescence, abscission and ethylene biosynthesis" J. Exp. Botany. 56:1007-16 (2005).
Wang et al., "An in vivo experimental system to study sugar phloem unloading in ripening grape berries during water deficiency stress," Annals of Botany, 92:523-8 (2003).
Wang et al., "Ethylene biosynthesis and signaling networks," The Plant Cell, Supplement 2002, S131-S151 (2002).
Wang et al., "Regulation of ethylene gas biosynthesis by the *Arabidopsis* ETI protein" Nature. 428:945-50 (2004).
Watanabe et al., "Screening, Isolation and Taxonomical Properties of Microorganisms Having Acrylonitrile Hydrating Activity" Agric. Biol. Chem. 51:3193-9 (1987).
Watkins and Frenkel, "Inhibition of pear fruit ripening by mannose," Plant Physiol. 85:56-61 (1987).
Weingart and Volksch, "Ethylene production by Pseudomonas syringae pathovars in vitro and in planta." Appl. Environ. Microbiol. 63:156-161 (1997).
Whittaker et al., "Expression of ethylene biosynthetic genes in Actinidia chinensis fruit" Plant Molec. Biol. 343:45-55 (1997).
Wild, "Controlled atmosphere update: a cost benefit analysis—horses for courses," Intermodal 1998 Conference, Dec. 103, 1998, Rotterdam. www.drwild.de/1998-12-02_Intermodal_CA.pdf.
Wolf M, et al. "Stabilisation and determination of the biological activity of L-asparaginase in poly(D,L-lactide-co-glycolide) nanospheres." Int J Pharm. Apr. 30, 2003;256(1-2):141-52.
Woolf et al., "I-MCP reduces physiological storage disorders of "Hass" avocados." Postharvest Biol. Technol. 35:43-60 (2005).
Woltering, "Interorgan translocation of 1-aminocyclopropane-1-carboxylic acid and ethylene coordinates senescence in emasculated Cymbidium flowers" Plant Physiol. 92:837-45 (1990).
Woodson et al., "Expression of ethylene biosynthetic pathway transcripts in senescing carnation flowers" Plant Physiol. 99:526-532 (1992).
Woodson and Lawton, "Ethylene-induced gene expression in carnation petals" Plant Physiol. 87:498-503 (1988).
Worthington Enzyme Manual. Asparaginase. Worthington Biochemical Corporation. 2012.
Yamada et al., "Optimum culture conditions for production by Pseudomonas chloroaphis B23 of nitrile hydratase" Agric. Biol. Chem. 50(11):2859-65 (1986).
Yamaki, T., et al., "Cloning and Sequencing of a Nitrile Hydratase Gene from Pseudonocardia thermophile, JCM3095," Journal of Fermentation and Bioengineering, vol. 83, No. 5, 1997, pp. 474-477.
Yang and Hoffman, "Ethylene biosynthesis and its regulationin higher plants" Ann. Rev. Plant Physiol. 35:155-89 (1984).
Zhao et al., "Elicitor signal transduction leading to production of plant secondary metabolites," Biotechnology Advances 23:283-333 (2005).
International Search Report and Written Opinion for related International Application No. PCT/US2014/026371, dated Jul. 9, 2014.
Reddy et al., "Biological control of Aspergillus flavus growth and subsequent aflatoxin B1 production in sorghum grains", African Journal of Biotechnology, vol. 9, No. 5, pp. 4247-4250 2010.

(56) References Cited

OTHER PUBLICATIONS

Gupta et al., "Purification and characterization of a novel antifungal endo-type chitosanase from Anabaena fertilissima", Annals of Microbiology, vol. 62, No. 3, pp. 1089-1098.
Extended European Search Report issued in European Application No. 14774584.8 dated Jul. 16, 2016.
Perry, Enhancing the Expression of Enzymes Used to Degrade Hydrocarbons and Cyanohydrins in *Rhodococcus* sp. DAP 96253 by Using Inducers such as Cobalt, Urea, and Propylene Gas; Also Enhances the Ability of the Bacteria to Delay the Ripening of Several Fruit Species, Biology Dissertations, Nov. 28, 2012.
Pierce et al., Preliminary report on a catalyst derived from induced cells ofstrain DAP 96253 that delays the ripening of selected climacteric fruit: bananas, avocados, and peaches, Journal of Industrial Microbiology & Biotechnology, 38:1567-1573, 2011.
Swensen, Induction of Cyanide Metabolizing Enzymes and Production of Antifungal Compounds by *Rhodococcus* Species Recommended Citation', Dissertation Biology, Georgia State University, 1-101,2013.
Office Action issued by the Japanese Patent Office for application 2016-502117, dated Nov. 21, 2017.
Official Action issued in Russian Application No. 2013105714/10(008509), dated Dec. 14, 2016.

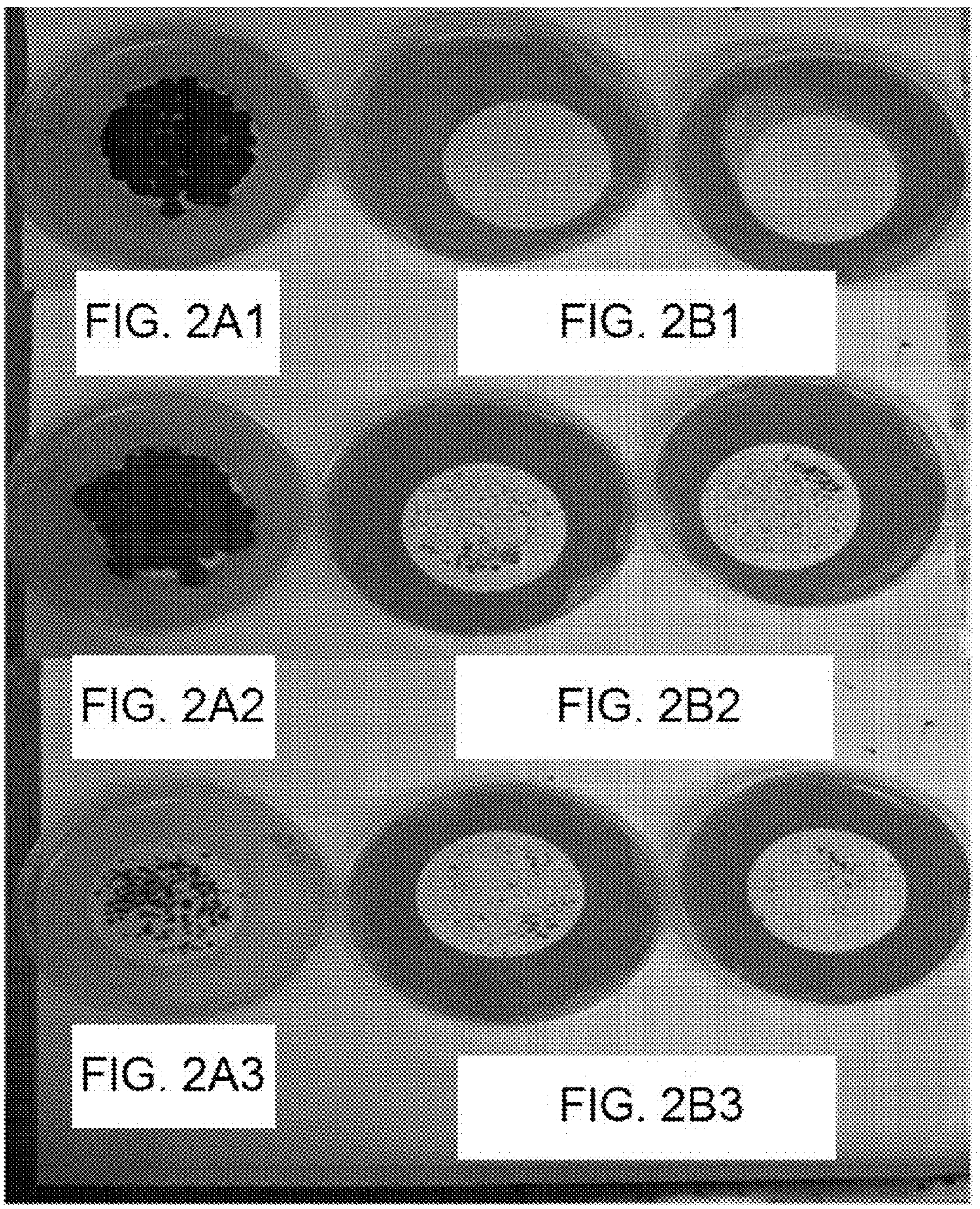
FIG. 2A1
FIG. 2B1
FIG. 2A2
FIG. 2B2
FIG. 2A3
FIG. 2B3

INHIBITING OR REDUCING FUNGAL GROWTH

CROSS-REFERENCE TO RELATED APPLICATIONS

This application is a divisional of co-pending Application Ser. No. 14/773,867, which was the National Stage of International Application No. PCT/US2014/026371, filed Mar. 13, 2014, which claims the benefit of U.S. Provisional Application No. 61/783,395, filed Mar. 14, 2013, and U.S. Provisional Application No. 61/783,573, filed Mar. 14, 2013, all of which are hereby incorporated herein by reference in their entireties.

BACKGROUND

Fungi can be detrimental to many different facets of life. For example, fungi (e.g., mildew or mold) can negatively affect aesthetics or human living conditions, e.g., through degradation/deterioration of material, through contamination, by making material, e.g., wood, appear undesirable, or through production of undesirable toxins. By way of another example, fungi can be detrimental on fruits and vegetables, as entire harvests of a fruit or vegetable could be wiped out by the growth of a fungus, e.g., through contamination and/or production of undesirable toxins.

Many fungi respond to ethylene, often with spore germination being a fungal ethylene response mechanism. While some fungi are known to produce ethylene, many more fungi do not synthesize ethylene but can still respond to ethylene. Methods targeting the response to ethylene or production of ethylene in fungi could therefore be targeted to inhibit or reduce fungal growth.

SUMMARY

Provided herein are methods and compositions for inhibiting or reducing fungal growth. The methods comprise exposing the plant or plant part to one or more bacteria, one or more enzymes, an enzymatic extract isolated from one or more bacteria, or any combination thereof, in a quantity sufficient to inhibit or reduce fungal growth at the location. The one or more bacteria can be selected from the group consisting of genus *Rhodococcus*, genus *Brevibacterium*, genus *Pseudonocardia*, genus *Nocardia*, genus *Pseudomonas*, and combinations thereof. The one or more enzymes can be selected from the group consisting of nitrile hydratases, amidases, asparaginases, ACC deaminases, cyanoalanine synthase-like enzymes, monooxygenases, dioxygenases, cyandiases, and combinations thereof.

The details of one or more aspects are set forth in the accompanying drawings and description below. Other features, objects, and advantages will be apparent from the description and drawings and from the claims.

DESCRIPTION OF DRAWINGS

FIG. 2A1 to 2B3 show exposure of *Cladosporium* sp. spores to *R. rhodochrous* cells grown under selected conditions. FIG. 2A1/2B1 shows the results when a defined number of spores of *Cladosporium* sp. were retained on 0.2 micron filters and the filters containing the fungal spores were then placed onto various media as follows: *Cladosporium* sp. spores on fungal growth medium without *Rhodococcus* present (2A1) and on a medium for delayed ripening activity containing *Rhodococcus* cells (2B1), FIG. 2A2/2B2 shows filter containing the *Cladosporium* sp. spores on a fungal spore recovery medium (2A2), without *Rhodococcus* present, and on partially induced medium (2B2) containing *Rhodococcus* cells, and FIG. 2A3/2B3 shows a filter containing *Cladosporium* sp. spores on a *Rhodococcus* growth medium without *Rhodococcus* present (2A3) and on with *Rhodococcus* present on the same growth medium, which is partially inducing the *Rhodococcus* Cells (2B3). The induced *R. rhodochrous* DAP 96253 cells clearly inhibited the germination of the *Cladosporium* sp. spores.

In FIGS. 3A and 3B, *Rhodococcus* were placed in a sector containing a growth medium which induced the *Rhodococcus* cells. In the other sectors, a defined number of *Fusarium* sp. spores were placed in a medium which supported *Fusarium* spore germination and mycelia growth. *Fusarium* spore germination was completely inhibited after 6 days. In FIGS. 3C and 3D, the *Rhodococcus* cells were placed in a medium which supported growth but which did not induce the *Rhodococcus* cells. As in FIGS. 3A and 3B, the *Fusarium* spores were placed onto a medium supportive of spore germination and mycelia growth. It is apparent from FIGS. 3C and 3D that non-induced *Rhodococcus* cells did not inhibit spore germination and fungal growth of *Fusarium*. The *Fusarium* spores were inoculated on SAB media in separate compartment on all the plates.

FIG. 4A shows the growth of *Fusarium* exposed to induced cells *Rhodococcus* in phosphate buffer. FIG. 4B shows a control of non-inducing, growth medium for non-induced *Rhodococcus*. FIGS. 4C and 4D shows the growth of *Fusarium* exposed to sub-induced *Rhodococcus* in phosphate buffer. Fully induced *Rhodococcus* cells inhibited the growth of *Fusarium* sp.

FIGS. 19A and 19B are controls. FIGS. 19C and 19D shows fungal growth and *Rhodococcus* un-induced and induced with cobalt, respectively.

FIGS. 20A and 20B are controls. FIGS. 20C and 20D show *Rhodococcus* induced with urea and cobalt urea, respectively. Fungal growth is inhibited FIG. 22 shows effect of cyanide production on *Fusarium* sporulation.

DETAILED DESCRIPTION

Figure 1A:
FIGS. 1A and 1B show a comparison, at Day 6, between commercially prepared peaches (with fungicide and wax treatments) (FIG. 1A) with non-processed peaches (containing no fungicide or wax coating) that have been placed in wrapping paper containing catalyst (FIG. 1B). The catalyst treated peaches were free of visible mold growth, whereas the fungicide treated peaches showed significant mold growth.

As used herein, the singular forms "a", "an", "the", include plural referents unless the context clearly dictates otherwise.

Throughout the specification the word "comprising," or grammatical variations thereof, will be understood to imply the inclusion of a stated element, integer or step, or group of elements, integers or steps, but not the exclusion of any other element, integer or step, or group of elements, integers or steps.

The disclosed compositions, apparatuses, and methods arise from the surprising finding that one or more bacteria are capable of inhibiting or reducing fungal growth. Optionally, the bacteria are induced to produce one or more enzymes capable of inhibiting or reducing fungal growth. Optionally, as described herein the specific enzymatic activity of one or more enzymes are capable of inhibiting or reducing fungal growth. As used throughout, fungal growth includes all stages of the life cycle of a fungus including, but not limited to, spore germination, mycelium growth and development, and the development and formation of fruiting structures on the fungus.

Provided herein are methods and compositions for inhibiting or reducing fungal growth. The methods comprise exposing a location to a composition comprising one or more bacteria, wherein the one or more bacteria are selected from the group consisting of genus *Rhodococcus*, genus *Brevibacterium*, genus *Pseudonocardia*, genus *Nocardia*, genus *Pseudomonas* and combinations thereof, and wherein the one or more bacteria are provided in a quantity sufficient to inhibit or reduce fungal growth at a location. Optionally, the bacteria are induced to produce one or more enzymes. In some embodiments, the methods comprise exposing a location to a composition comprising one or more enzymes selected from the group consisting of nitrile hydratases, amidases, asparaginases, ACC deaminases, cyanoalanine synthase-like enzymes, monooxygenases, dioxygenases, cyanidases, and combinations thereof, wherein the enzymes are provided in a quantity sufficient to inhibit or reduce fungal growth at the location.

The methods and compositions are drawn to inhibiting or reducing fungal growth at a location. Alternatively or additionally, the methods and compositions inhibit or reduce toxin development or release by a fungus. As defined herein, "inhibiting or reducing fungal growth," and grammatical variants thereof, refers to any slowing, interruption, suppression, delay, or inhibition of the fungal growth. Inhibiting or reducing fungal growth can, for example, comprise inhibiting or reducing growth of resting fungal cells, which can include spore germination, mycelia development, and/or the formation of fruiting structures on the fungus (e.g., sporangia/sporophores). Fungal growth can, for example, be produced by a fungus selected from the group consisting of mold, yeast, mildew, fungi that cause smut, fungi that cause rust, fungi that cause diseases of plants, and fungi that cause diseases of animals. Optionally, the fungus is selected from the group consisting of *Trichoderma* sp., *Aspergillus niger, Aspergillus flavus, Aspergillus fumigatis, Alternaria alternate, Epicoccum nigrum, Pichia pastoris, Geomyces destructans, Geomyces asperulatus*, and *Geomyces pannorum*. By way of an example, inhibiting or reducing fungal growth can result in slowing or inhibiting the growth of a fungus on any object susceptible to fungal growth (e.g., an inorganic surface or a medical device). By way of another example, inhibiting or reducing fungal growth can result in slowing or inhibiting the growth of a fungus on a plant or plant part.

As defined herein a location is anywhere a fungus may grow, e.g., a location susceptible to fungal growth. A location can be an object (e.g., an inanimate object) or a material. An object or a material can be selected from the group consisting of a counter top, bathtub or shower (or other surface exposed to moisture), cardboard box, an inorganic surface (e.g., a glass surface, a tile surface, a metal surface, a wood surface), paper wrapping, plastic wrapping, wax paper, metal can, sheetrock, wallboard, wood, a medical device, and surgical dressing. The location can, for example, comprise a plant or plant part. By way of an example, the methods and compositions described herein can inhibit or reduce fungal growth on or near a plant or plant part.

As used herein, "plant" or "plant part" is broadly defined to include intact plants and any part of a plant. Optionally, the plant or plant part is consumable. Examples of plants or plant parts include but are not limited to fruit, vegetables, flowers, seeds, leaves, nuts, embryos, pollen, ovules, branches, kernels, ears, cobs, husks, stalks, roots, root tips, anthers, saplings, and the like. In other embodiments, the plant part is a fruit, vegetable, or flower (including cut flowers). Optionally, the plant or plant part is a consumable product or food, for example, a seed, e.g., nuts, legumes, cereals, or coffees, fruit or vegetable. Optionally, the plant or plant part is directly consumable or indirectly consumable. As used herein, indirectly consumable plants or plant parts refers to plants or plant parts used to make a consumable product or food, e.g., coffee seeds or oil seeds.

In certain embodiments, provided are methods and compositions for inhibiting or reducing fungal growth on a fruit and/or a vegetable. A "fruit" or "vegetable" can include, but is not limited to, apples, apricots, asparagus, avocados, bananas, beans, cabbage, cantaloupe, cucumbers, eggplant, grapefruit, grapes, honeydew melons, lemons, lettuce, lima beans, limes, mangos, nectarines, okra, broccoli, oranges, papayas, peaches, peppers, pineapples, potatoes, pumpkins, soybeans, spinach, summer squash, sweet potatoes, tomatoes, watermelons, winter squash, and zucchini.

In certain embodiments, provided are methods and compositions for inhibiting or reducing fungal growth on a flower. A "flower" can include, but is not limited to, carnation, rose, orchid, portulca, malva, begonia, anthurium, cattleyas, and poinsettias.

In certain embodiments, provided are methods and compositions for inhibiting or reducing fungal growth in grain. Optionally, the fungal growth is inhibited or reduced by inhibition of spore germination. Grains are seeds (with or without hull or fruit layers attached) harvested for human food or animal feed. Optionally, the grain is a cereal grain, a starchy grain, a grain legume or an oilseed. Cereal grains include, but are not limited to, maize or corn, sorghum, fonio, millet, e.g., pearl millet, proso millet, finger millet, foxtail millet, Japanese millet, kodo millet, Job's tears, rice, rye, barley, oat, triticale, wild rice, and teff. Starchy grains include, but are not limited to, amaranth, quinoa and buckwheat. Grain legumes includes but are not limited to soybean, common bean, chickpea, lima bean, runner bean, pigeon pea, lentil, field pea or garden pea, lupin, mung bean, fava bean, and peanut. Oilseeds includes but are not limited to, rapeseed (including canola), India mustard, black mustard, sunflower seed, safflower, flax seed (Flax family), hemp seed (Hemp family), and poppyseed (Poppy family). Optionally, the compositions comprising one or more bacteria or one or more enzymes are exposed to the grain in the field prior to or during harvesting of the grain. Optionally, the compositions are applied, e.g., coated, to grain or other seeds prior to planting.

In certain embodiments, the methods and compositions for inhibiting or reducing fungal growth comprises exposing the location to one or more bacteria selected from the group consisting of genus *Rhodococcus*, genus *Brevibacterium*, genus *Pseudomonas*, genus *Nocardia*, genus *Pseudonocardia* and combinations thereof. The one or more bacteria can, for example, include *Rhodococcus* spp. The *Rhodococcus* spp can, for example, include *Rhodococcus rhodochrous* DAP 96253 strain, *Rhodococcus rhodochrous* DAP 96622 strain, *Rhodococcus erythropolis*, or combinations thereof. Optionally, the compositions comprise *Rhodococcus rhodochrous* and *Rhodococcus erythropolis*. Exemplary organisms include, but are not limited to, *Pseudomonas chloroaphis* (ATCC 43051) (Gram-negative), *Pseudomonas chloroaphis* (ATCC 13985) (Gram-negative), *Rhodococcus erythropolis* (ATCC 47072) (Gram-positive), and *Brevibacterium ketoglutamicum* (ATCC 21533) (Gram-positive). Examples of *Nocardia* and *Pseudonocardia* species have been described in European Patent No. 0790310; Collins and Knowles J. Gen. Microbiol. 129:711-718 (1983); Harper Biochem. J. 165:309-319 (1977); Harper Int. J. Biochem. 17:677-683 (1985); Linton and Knowles J Gen. Microbiol. 132:1493-1501 (1986); and Yamaki et al., J. Ferm. Bioeng. 83:474-477 (1997).

Although in some embodiments the one or more bacteria are selected from the group consisting of *Rhodococcus* spp., *Brevibacterium ketoglutamicum*, and *Pseudomonas chloroaphis*, any bacterium that inhibits or reduces fungal growth when exposed to location can be used in the present methods. For example, bacteria belonging to the genus *Nocardia* [see Japanese Patent Application No. 54-129190], *Rhodococcus* [see Japanese Patent Application No. 2-470], *Rhizobium* [see Japanese Patent Application No. 5-236977], *Klebsiella* [Japanese Patent Application No. 5-30982], *Aeromonas* [Japanese Patent Application No. 5-30983], *Agrobacterium* [Japanese Patent Application No. 8-154691], *Bacillus* [Japanese Patent Application No. 8-187092], *Pseudonocardia* [Japanese Patent Application No. 8-56684], *Burkholderia, Corynebacterium*, and *Pseudomonas* are non-limiting examples of bacteria that can be used. Not all species within a given genus exhibit the same type of enzyme activity and/or production. Thus, it is possible to have a genus generally known to include strains capable of exhibiting a desired activity but have one or more strains that do not naturally exhibit the desired activity or one or more strains which do not exhibit the activity when grown on the same medium as the species which exhibit this activity. Thus, host microorganisms can include strains of bacteria that are not specifically known to have the desired activity but are from a genus known to have specific strains capable of producing the desired activity. Such strains can have transferred thereto one or more genes useful to cause the desired activity. Non-limiting examples of such strains include *Rhodococcus equi* and *Rhododoccus globerulus* PWD1.

Further, specific examples of bacteria include, but are not limited to, *Nocardia* sp., *Rhodococcus* sp., *Rhodococcus rhodochrous, Klebsiella* sp., *Aeromonas* sp., *Citrobacter freundii, Agrobacterium rhizogenes, Agrobacterium tumefaciens, Xanthobacter flavas, Erwinia nigrifluens, Enterobacter* sp., *Streptomyces* sp., *Rhizobium* sp., *Rhizobium loti, Rhizobium legminosarum, Rhizobium merioti, Pantoea agglomerans, Klebsiella pneumoniae* subsp. *pneumoniae, Agrobacterium radiobacter, Bacillus smithii, Pseudonocardia thermophila, Pseudomonas chloroaphis, Rhodococcus erythropolis, Brevibacterium ketoglutamicum*, and *Pseudonocardia thermophila*. Optionally, the microorganisms used can, for example, comprise *Rhodococcus rhodochrous* DAP 96253 and *Rhodococcus rhodochrous* DAP 96622, and combinations thereof.

As used herein, exposing the location to one or more bacteria includes, for example, exposure to intact bacterial cells, bacterial cell lysates, and bacterial extracts that possess enzymatic activity (i.e., "enzymatic extracts"). Methods for preparing lysates and enzymatic extracts from cells, including bacterial cells, are routine in the art. Optionally, the one or more bacteria or enzymatic extracts are fixed with glutaraldehyde and crosslinked. Optionally, the crosslinked, glutaraldehyde-fixed bacteria or extract is formulated with a carrier into a spray.

In certain embodiments, the methods and compositions for inhibiting or reducing fungal growth comprise exposing the location to an enzyme. The enzyme can be selected from the group consisting of nitrile hydratase, amidase, asparaginase, ACC (1-aminocyclopropane-1-carboxylic acid) deaminase, cyanoalanine synthase-like enzyme, alkane monooxygenase, ammonium monooxygenase, methane monooxygenase, toluene dioxygenase, cyanidase, and/or a combination thereof. The enzyme can be provided within a composition for exposure to the location. The enzyme can also be a purified enzyme or can be provided as an enzymatic extract as described above. Optionally, the methods for inhibiting or reducing fungal growth at a location comprise exposing the location to a composition comprising an enzyme, the enzyme being selected from one or more of nitrile hydratase, amidase, asparaginase, ACC deaminase, cyanoalanine synthase-like enzyme, alkane monooxygenase, ammonium monooxygenase, methane monooxygenase, toluene dioxygenase, and cyanidase. The one or more bacteria, enzymatic extract, or enzymes used in the methods may at times be more generally referred to herein as the "catalyst."

In the methods provided herein, the location is exposed to one or more bacteria, one or more enzymes, enzymatic extract isolated from or derived from the one or more bacteria, or any combination thereof, in a quantity sufficient to inhibit or reduce fungal growth. In some embodiments, the plant or plant part is exposed to one or more bacteria in combination with one or more exogenous enzymes and/or enzymatic extracts. "Exogenous" refers to enzymes or enzymatic extracts that are isolated and/or purified ex situ and is distinguished from enzymes produced by bacteria in situ. This combined exposure can take place simultaneously and/or sequentially. For example, the plant can be exposed to exogenous enzymes and/or enzymatic extracts 1 to 60 minutes, 1 to 24 hours, or 1 to 7 days after exposure to the bacteria.

"Exposing" a location to one or more bacteria, one or more enzymes, and/or an enzymatic extract includes any method of presenting a bacterium, enzyme, and/or extract to the location. Optionally, the location is indirectly exposed to the one or more bacteria, one or more enzymes, and/or the enzymatic extract. Indirect methods of exposure include, for example, placing the one or more bacteria, one or more enzymes, and/or enzymatic extract in the general proximity of the location (i.e., indirect exposure). Optionally, the location is directly exposed to one or more bacteria, one or more enzymes, and/or the enzymatic extract, whereby the one or more bacteria, one or more enzymes, and/or enzymatic extract are in direct contact with the location.

In certain embodiments, exposure of the bacteria, enzyme, and/or the enzymatic extract isolated from the bacteria can occur, for example, by providing the bacteria, enzyme, and/or enzymatic extract in liquid form and spraying it onto or near the location. The bacteria, enzyme, and/or enzymatic extract can, for example, further comprise a liquid carrier. Liquid carriers can be selected from the group consisting of an aromatic hydrocarbon, a substituted naphthalene, a phthalic acid ester, an aliphatic hydrocarbon, an alcohol, and a glycol. Optionally, the liquid carrier can be a wax or similar type material coating, which could be applied to the plant as a liquid, but would be solid at ambient or lower temperatures. Optionally, the bacteria, enzyme and/or enzymatic extract are provided onto or near the location by a fog or spray. For example, the bacteria, enzyme or enzymatic extract can be provided to the soil in the area where the fungi is to be controlled.

In certain embodiments, exposure of the one or more bacteria, one or more enzymes, and/or the enzymatic extract isolated from the bacteria can occur, for example, by providing the bacteria, enzyme, and/or enzymatic extract in solid form and dusting it onto or near the location. The bacteria, enzyme, and/or enzymatic extract can, for example, further comprise a solid carrier. The solid carrier can be selected from the group consisting of a dust, a wettable powder, a water dispersible granule, and mineral fillers. Optionally, the solid carrier is a mineral filler. Mineral fillers can, for example, be selected from the group consisting of a calcite, a silica, a talc, a kaolin, a montmorillonite, and an attapulgite. Other solid supports for use with the bacteria, enzyme, and/or enzymatic extract are described herein.

In certain embodiments, exposure of the one or more bacteria, one or more enzymes, and/the enzymatic extract isolated from the bacteria can occur, for example, by providing the bacteria, enzyme, and/enzymatic extract as a composition including iron or another magnetic material. Iron-based compositions including ferrous metal matrices possess a magnetic attraction and can be used to deliver the bacteria, enzymes and/enzymatic extracts to materials, e.g., crops that are filtered or cleaned using a magnet. This process advantageously removes any unwanted metal pieces from the grain in addition to removing the provided compositions comprising the bacteria, enzymes or enzymatic extracts. By way of example, the one or more bacteria, one or more enzymes, or the enzymatic extract isolated from the bacteria can be applied to the grain, e.g., the grain crop, in the form of a spray. The grain crop is then harvested and the harvested grain is then processed through a machine or apparatus comprising a magnet to filter or clean the harvested grain and remove unwanted metal pieces as well as compositions comprising the bacteria, enzymes and/enzymatic extracts from the harvested grain.

In certain embodiments, the one or more bacteria, one or more enzymes, and/or enzymatic extract further comprise a coating, wherein the coating makes the one or more bacteria, one or more enzymes, and/or enzymatic extract water resistant. The coating can be selected from a hydrophobic fatty acid polyester coating or a wax. Optionally, the hydrophobic fatty acid polyester coating is a long chain fatty acid polyester derived from sucrose, sorbitol, sorbinose, glycerol, or raffinose.

Also provided herein are compositions for inhibiting or reducing fungal growth. The compositions can, for example, comprise one or more bacteria, one or more enzymes, and/or one or more enzymatic extracts capable of inhibiting or reducing fungal growth. The compositions can further comprise solid, liquid, and gelatinous carriers, as disclosed above, and/or media and media components for inducing and stabilizing the one or more bacteria, one or more enzymes, and/or enzymatic extracts, as disclosed below. Optionally, the compositions can be converted into pellet form for distribution or application to the plant or plant part.

Optionally, the one or more bacteria, one or more enzymes, and/or enzymatic extract are used in combination with other agents that inhibit or reduce fungal growth. For example, the provided methods can further comprise the step of exposing the plant or plant part to a agent that inhibits or reduces fungal growth, e.g., a fungicide. Likewise, the provided compositions can further comprise an agent that inhibits or reduces fungal growth, e.g., a fungicide. Agents that inhibit or reduce fungal growth include, but are not limited to, anthocyanins, organic acids, such as, propionic acid and sorbic acid, aluminosilicates, clays, zeolites, and calcium propanoate.

As defined herein, a "sufficient" quantity or effective amount of the bacteria, enzyme, and/or enzymatic extract will depend on a variety of factors, including, but not limited to, the particular bacteria, enzyme, and/or enzymatic extract utilized in the method, the form in which the bacteria is exposed to the location (e.g., as intact bacterial cells (dead or alive), cell lysates, enzymatic extracts, and/or enzymes as described above), the means by which the bacteria, enzyme, and/or enzymatic extract is exposed to the location, the length of time of the exposure, and the type and amount of fungal signal compounds that result in the inhibition or reduction of fungal growth. Optionally, the quantity of bacteria exposed to the location is in the range of 1 to 250 mg of cell-dry weight or the equivalent thereof for enzymatic extracts and enzymes. For 1 mg of dry weight of cells, typically there are 150-300 units of nitrile hydratase, 10-25 units of amidase, 7-15 units of cyanidase, 7-20 units of ACC deaminase, and 7-20 units of cyanoalanine synthase-like enzyme. By way of other examples, the quantity of bacteria exposed to the location is in the range of 0.1 mg to 1 g, 0.1 to 400 mg, 1 to 200 mg, 1 to 80 mg, or 1 to 10 mg of cell-dry weight or the equivalent thereof for enzymatic extracts and enzymes. By way of example, the quantity of bacteria exposed to the location is, for example, in the range of 0.1 mg to 1 g per 9-10 kilos (kg) of plant or plant part. It would be a matter of routine experimentation for the skilled artisan to determine the "sufficient" quantity of the one or more bacteria, one or more enzymes, or enzymatic extract necessary to inhibit or reduce fungal growth. For example, if the bacteria, one or more enzymes, or enzymatic extract necessary to inhibit or reduce fungal growth are immobilized or stabilized, the quantity of bacteria, one or more enzymes, or enzymatic extract is adjusted to inhibit or reduce fungal growth.

In certain embodiments, the one or more bacteria are "induced" to exhibit a desired characteristic (e.g., the expression of a desired level of activity of an enzyme of the bacteria) by exposure or treatment with a suitable inducing agent. Inducing agents include, but are not limited to urea, methyl carbamate, cobalt, asparagine, glutamine, and combinations thereof. Optionally, the one or more bacteria are exposed to or treated with urea, methyl carbamate, methacrylamide, or acetamide. Optionally, the one or more bacteria are exposed to or treated with a mixture of inducing agents comprising urea or methyl carbamate and one or more of asparagine and cobalt. In some embodiments, the compositions and methods optionally exclude an inducing agent, such as cobalt.

The inducing agent, when used, can be added at any time during cultivation of the desired cells. For example, with respect to bacteria, the culture medium can be supplemented with an inducing agent prior to beginning cultivation of the bacteria. Alternately, the bacteria could be cultivated on a medium for a predetermined amount of time to grow the bacteria and the inducing agent could be added at one or more predetermined times to induce the desired enzymatic activity in the bacteria. Moreover, the inducing agent could be added to the growth medium (or to a separate mixture including the previously grown bacteria) to induce the desired activity in the bacteria after the growth of the bacteria is completed or during a second growth or maintenance phase.

While not intending to be limited to a particular mechanism, "inducing" the bacteria may result in the production or activation (or increased production or increased activity) of one or more of enzymes, such as nitrile hydratase, amidase, asparaginase, ACC deaminase, cyanoalanine synthase-like enzyme, alkane monooxygenase, ammonium monooxygenase, methane monooxygenase, toluene dioxygenase, and/or cyanidase, and the induction of one or more of these enzymes may play a role in inhibiting or reducing fungal growth. "Nitrile hydratases," "amidases," "asparaginases," "ACC deaminases," "cyanoalanine synthase-like enzymes," "AMO-type (alkane or ammonium) monooxygenases," "methane monooxygenases," "toluene dioxygenases," and "cyanidases" comprise families of enzymes present in cells from various organisms, including but not limited to, bacteria, fungi, plants, and animals. Such enzymes are well known, and each class of enzyme possesses recognized enzymatic activities.

The methods of inducing an enzymatic activity can be accomplished without the requirement of introducing hazardous nitriles, such as acrylonitrile, into the environment. Previously, it was believed that induction of specific enzyme activity in certain microorganisms required the addition of chemical inducers. For example, in the induction of nitrile hydratase activity in *Rhodococcus rhodochrous* and *Pseudomonas chloroaphis*, it was generally believed to be necessary to supplement with hazardous chemicals, such as acetonitrile, acrylonitrile, acrylamide, and the like. However, enzymatic activity in nitrile hydratase producing microorganisms can be induced with the use of non-hazardous media additives, such as amide containing amino acids and derivates thereof, and optionally stabilized with trehalose. Optionally, asparagine, glutamine, or combinations thereof, can be used as inducers. Methods of inducing and stabilizing enzymatic activity in microorganisms are described in U.S. Pat. No. 7,531,343 and U.S. Pat. No. 7,531,344, which are incorporated herein by reference.

The disclosed methods of inducing enzymatic activity provide for the production and stability of a number of enzymes using modified media, immobilization, and stabilization techniques, as described herein. For example, enzymatic activity can be induced and stabilized through use of media comprising amide-containing amino acids, or derivatives thereof, and, optionally stabilized by, trehalose. In some embodiments, the methods of induction and stabilization comprise culturing a nitrile hydratase producing microorganism in a medium comprising one or more amide containing amino acids or derivatives thereof, and, optionally, trehalose. Optionally, disclosed are methods for inducing nitrile-hydratase using a medium supplemented with amide containing amino acids or derivatives thereof, which preferably include asparagine, glutamine or a combination thereof. Optionally, disclosed are methods for inducing nitrile-hydratase using a nutritionally complete medium supplemented with only asparagine. Optionally, disclosed are methods for inducing nitrile-hydratase using a nutritionally complete medium supplemented with only glutamine. Optionally, disclosed are methods for stabilizing nitrile-hydratase using a nutritionally complete medium supplemented with only trehalose. More particularly, the methods of induction and stabilization comprise culturing the microorganism in the medium and optionally collecting the cultured microorganisms or enzymes produced by the microorganisms.

Induction and stabilization of enzymes can be achieved without the use of hazardous nitriles. However, while the induction methods eliminate the need for hazardous chemicals for enzyme activity induction, the use of such further inducers is not excluded. For example, one or more nitriles could be used to assist in specific activity development. Media supplemented with succinonitrile and cobalt can be useful for induction of enzymes, including, for example, nitrile hydratase, amidase, asparaginase I, ACC deaminase, cyanoalanine synthase-like enzyme, alkane monooxygenase, ammonium monooxygenase, methane monooxygenase, toluene dioxygenase, and cyanidase. However, the use of nitriles is not necessary for induction of enzyme activity. While the use of nitriles and other hazardous chemicals is certainly not preferred, optionally, such use is possible.

Stabilization of enzyme activity can be achieved through immobilization methods, such as affixation, entrapment, and cross-linking, thereby, extending the time during which enzyme activity can be used. Thus, in some embodiments, induction methods and methods of delaying a chill injury response further comprise at least partially immobilizing the microorganism. Stabilization can be provided by immobilizing the enzymes, enzymatic extracts, or microorganisms producing the enzymes or enzymatic extracts. For example, enzymes or enzymatic extracts harvested from the microorganisms or the induced microorganisms themselves can be immobilized to a substrate as a means to stabilize the induced activity. Optionally, the nitrile hydratase producing microorganisms are at least partially immobilized. Optionally, the enzymes or microorganisms are at least partially entrapped in or located on the surface of a substrate. This allows for presentation of an immobilized material with induced activity (e.g., a catalyst) in such a manner as to facilitate reaction of the catalyst with an intended material and recovery of a desired product while simultaneously retaining the catalyst in the reaction medium and in a reactive mode. In certain embodiments, the stabilization through immobilization methods, such as affixation and entrapment, of the one or more bacteria kills or inactivates the one or more bacteria. Thus, optionally, the induced microorganisms used in the present methods are dead (killed) or inactivated, but are still capable of exhibiting catalyst activity.

Any substrate generally useful for affixation of enzymes, enzymatic extracts, or microorganisms can be used. Optionally, the substrate comprises alginate or salts thereof. Alginate is a linear copolymer with homopolymeric blocks of (1-4)-linked L-D-mannuronate (M) and its C-5 epimer L-L-guluronate (G) residues, respectively, covalently linked together in different sequences or blocks. The monomers can appear in homopolymeric blocks of consecutive G-residues (G-blocks), consecutive M-residues (M-blocks), alternating M and G-residues (MG-blocks), or randomly organized blocks. Optionally, calcium alginate is used as the substrate. The calcium alginate can, for example, be cross-linked, such as with polyethyleneimine, to form a hardened calcium alginate substrate. Further description of such immobilization techniques can be found in Bucke, "Cell Immobilization in Calcium Alginate," Methods in Enzymology, vol. 135, Part B (ed. K. Mosbach) pp. 175-189 (1987), which is incorporated herein by reference. The stabilization effect of immobilization using polyethylenimine cross-linked calcium alginate is discussed in U.S. patent application Ser. No. 11/695,377, filed Apr. 2, 2007, which is hereby incorporated by reference in its entirety.

Optionally, the substrate comprises an amide-containing polymer. Any polymer comprising one or more amide groups can be used. Optionally, the substrate comprises a polyacrylamide polymer.

Stabilization can further be achieved through cross-linking. For example induced microorganisms can be chemically cross-linked to form agglutinations of cells. Optionally, the induced microorganisms are fixed and cross-linked using glutaraldehyde. For example, microorganisms can be suspended in a mixture of de-ionized water and glutaraldehyde followed by addition of polyethylenimine until maximum flocculation is achieved. The cross-linked microorganisms (typically in the form of particles formed of a number of cells) can be harvested by simple filtration. Further description of such techniques is provided in Lopez-Gallego, et al., J. Biotechnol. 119:70-75 (2005), which is incorporated herein by reference. In certain embodiments, the cross-linking kills or inactivates the microorganism. Thus, optionally, the induced microorganisms used in the present methods are dead (killed) or inactivated, but are still capable of exhibiting catalyst activity.

Optionally, the microorganisms, enzymes, and/or enzymatic extracts can be encapsulated rather than allowed to remain in the classic Brownian motion. Such encapsulation facilitates collection, retention, and reuse of the microorganisms and generally comprises affixation of the microorganisms to a substrate. Such affixation can also facilitate stabilization of the microorganisms, enzymes, and/or enzymatic extracts as described above, or may be solely to facilitate ease of handling of the induced microorganisms, enzymes, or enzymatic extracts.

The microorganisms, enzymes, and/or enzymatic extracts can be immobilized by any method generally recognized for immobilization of microorganisms, enzymes, and/or enzymatic extracts such as sorption, electrostatic bonding, covalent bonding, and the like. Generally, the microorganisms, enzymes, and/or enzymatic extracts are immobilized or entrapped on a solid support which aids in the recovery of the microorganisms enzymes, or enzymatic extracts from a mixture or solution, such as a detoxification reaction mixture. Suitable solid supports include, but are not limited to, granular activated carbon, compost, wood or wood products, (e.g., paper, wood chips, wood nuggets, shredded pallets or trees), bran (e.g., wheat bran), metal or metal oxide particles (e.g., alumina, ruthenium, iron oxide), ion exchange resins, DEAE cellulose, DEAE-SEPHADEX® polymer, waxes/coating materials (such as those used as a coating for fruits and vegetables and inanimate surfaces), ceramic beads, cross-linked polyacrylamide beads, cubes, prills, or other gel forms, alginate beads, L-carrageenan cubes, as well as solid particles that can be recovered from the aqueous solutions due to inherent magnetic ability. The shape of the catalyst is variable (in that the desired dynamic properties of the particular entity are integrated with volume/surface area relationships that influence catalyst activity). Optionally, the induced microorganism is immobilized in alginate beads that have been cross-linked with polyethyleneimine or is immobilized in a polyacrylamide-type polymer.

In some embodiments, the compositions and medium used in the induction and stabilization methods further comprise one or more amide containing amino acids or derivatives thereof, and/or trehalose. The amide containing amino acids can, for example, be selected from the group consisting of asparagine, glutamine, derivatives thereof, or combinations thereof. For example, the amide-containing amino acids may include natural forms of asparagine, anhydrous asparagine, asparagine monohydrate, or natural forms of glutamine, anhydrous glutamine, and/or glutamine monohydrate, each in the form of the L-isomer or D-isomer.

The concentration of the amide containing amino acids or derivatives thereof in the medium can vary depending upon the desired end result of the culture. For example, a culture may be carried out for the purpose of producing microorganisms having a specific enzymatic activity. Optionally, a culture may be carried out for the purpose of forming and collecting a specific enzyme from the cultured microorganisms. Optionally, a culture may be carried out for the purpose of forming and collecting a plurality of enzymes having the same or different activities and functions.

The amount of the amide containing amino acids, or derivatives thereof, added to the growth medium or mixture can generally be up to 10,000 parts per million (ppm) (i.e., 1% by weight) based on the overall weight of the medium or mixture. The induction methods are particularly beneficial, however, in that enzyme activity can be induced through addition of even lesser amounts. Optionally, the one or more amide containing amino acids are present at a concentration of at least 50 ppm. By way of other examples, the concentration of the amide containing amino acids or derivatives thereof is in the range of 50 ppm to 5,000 ppm, 100 ppm to 3,000 ppm, 200 ppm to 2,000 ppm, 250 ppm to 1500 ppm, 500 ppm to 1250 ppm, or 500 ppm to 1000 ppm.

In some embodiments, the stabilization methods include the use of trehalose. The concentration of trehalose in the compositions or medium used in the induction methods can be at least 1 gram per liter (g/L). Optionally, the concentration of trehalose is in the range of 1 g/L to 50 g/L, or 1 g/L to 10 g/L. Optionally, the concentration of trehalose in the medium is at least 4 g/L.

The amide containing amino acids or derivatives thereof and/or trehalose are added to a nutritionally complete media. A suitable nutritionally complete medium generally is a growth medium that can supply a microorganism with the necessary nutrients required for its growth, which minimally includes a carbon and/or nitrogen source. One specific example is the commercially available R2A agar medium, which typically consists of agar, yeast extract, proteose peptone, casein hydrolysate, glucose, soluble starch, sodium pyruvate, dipotassium hydrogenphosphate, and magnesium sulfate. Another example of a nutritionally complete liquid medium is Yeast Extract Malt Extract Agar (YEMEA), which consists of glucose, malt extract, and yeast extract (but specifically excludes agar). Also, media of similar composition, but of vegetable origin can be used for the disclosed methods. Any nutritionally complete medium known in the art could be used for the disclosed methods, the above media being described for exemplary purposes only. Such nutritionally complete media can be included in the compositions described herein.

Optionally, the disclosed compositions and media can contain further additives. Typically, the other supplements or nutrients are those useful for assisting in greater cell growth, greater cell mass, or accelerated growth. For example, the compositions and media can comprise a carbohydrate source in addition to any carbohydrate source already present in the nutritionally complete medium.

As described above, most media typically contain some content of carbohydrate (e.g., glucose); however, it can be useful to include an additional carbohydrate source (e.g., maltose or less refined sugars, such as dextrose equivalents that would be polymers of dextrose, or any carbohydrate that supports growth of the cell and induction of the desired activity). The type of excess carbohydrate provided can depend upon the desired outcome of the culture. For example, the addition of carbohydrates, such as maltose or maltodextrin, has been found to provide improved induction of asparaginase I. Additionally, the addition of carbohydrates, such as maltose or maltodextrin, potentially improves stability of enzymatic activity (e.g., nitrile hydratase activity).

In some embodiments, the compositions and media further comprise cobalt. Cobalt or a salt thereof can be added to the mixture or media. For example, the addition of cobalt (e.g., cobalt chloride) to the media can be particularly useful for increasing the mass of the enzyme produced by the cultured microorganisms. Cobalt or a salt thereof can, for example, be added to the culture medium such that the cobalt concentration is an amount up to 400 ppm. Cobalt can, for example, be present at a concentration of 5 ppm to 400 ppm, 10 ppm to 100 ppm, 10 ppm to 80 ppm, or 10 ppm to 25 ppm.

In some embodiments, the compositions and media further comprise urea. Urea or a salt thereof can be added to the mixture or media. Urea or a salt thereof can, for example, be added to the culture medium such that the urea concentration is in an amount up to 10 g/L. Urea can, for example, be present in a concentration of 5 g/L to 30 g/L, 5 g/L to 20 g/L, 5 g/L to 12 g/L, or 7 g/L to 10 g/L. Optionally, urea is present at a concentration of 7.5 g/L. Optionally, both urea and cobalt are added to the media.

The compositions and media may also include further components. For example, other suitable medium components may include commercial additives, such as cottonseed protein, maltose, maltodextrin, and other commercial carbohydrates. Optionally, the medium further comprises maltose or maltodextrin. Maltose or maltodextrin, for example, can be added to the culture medium such that the maltose or maltodextrin concentration is at least 1 g/L. Optionally, the compositions and media are free of any nitrile containing compounds. Nitrile compounds were previously required in the culture medium to induce enzyme activity toward two or more nitrile compounds. The compositions described herein achieve this through the use of completely safe trehalose and/or amide containing amino acids or derivatives thereof; therefore, the medium can be free of any nitrile containing compounds.

"Enzymatic activity," as used herein, generally refers to the ability of an enzyme to act as a catalyst in a process, such as the conversion of one compound to another compound. Likewise, the desired activity referred to herein can include the activity of one or more enzymes being actively expressed by one or more microorganisms. In particular, nitrile hydratase catalyzes the hydrolysis of nitrile (or cyanohydrin) to the corresponding amide (or hydroxy acid). Amidase catalyzes the hydrolysis of an amide to the corresponding acid or hydroxy acid. Similarly, an asparaginase enzyme, such as asparaginase I, catalyzes the hydrolysis of asparagine to aspartic acid. ACC deaminase catalyzes the hydrolysis of 1-aminocyclopropane-1-carboxylate to ammonia and L-ketobutyrate. Beta-cyanoalanine synthase catalyzes the formation of the non-protein amino acid cyanoalanine from cysteine and cyanide. Cyanidase catalyzes the hydrolysis of cyanide to ammonia and formate. Alkane or ammonium monooxygenase (AMO) and methane monooxygenase catalyze the hydrolysis of ethylene to ethylene epoxide. Toluene dioxygenase can, for example, oxidize ethylene, and is known as an AMO-like enzyme. Ethylene degradation activity results in the degradation of produced ethylene.

Activity can be referred to in terms of "units" per mass of enzyme or cells (typically based on the dry weight of the cells, e.g., units/mg cdw). A "unit" generally refers to the ability to convert a specific content of a compound to a different compound under a defined set of conditions as a function of time. Optionally, one "unit" of nitrile hydratase activity refers to the ability to convert 1 Lmol of acrylonitrile to its corresponding amide per minute, per milligram of cells (dry weight) at a pH of 7.0 and a temperature of 30° C. Similarly, one unit of amidase activity refers to the ability to convert 1 Lmol of acrylamide to its corresponding acid per minute, per milligram of cells (dry weight) at a pH of 7.0 and a temperature of 30° C. Further, one unit of asparaginase I activity refers to the ability to convert 1 Lmol of asparagine to its corresponding acid per minute, per milligram of cells (dry weight) at a pH of 7.0 and a temperature of 30° C. Further, one unit of ACC deaminase activity refers to the ability to convert 1 Lmol of 1-aminocyclopropane-1-carboxylate to ammonia and L-ketobutyrate per minute, per milligram of cells (dry weight) at a pH of 7.0 and a temperature of 30° C. Further, one unit of cyanoalanine synthase-like enzyme activity refers to the ability to convert 1 Lmol of cysteine and cyanide to cyanoalanine per minute, per milligram of cells (dry weight) at a pH of 7.0 and a temperature of 30° C. Further, one unit of cyanidase activity refers to the ability to convert 1 Lmol of cyanide to ammonia and formate per minute, per milligram of cells (dry weight) at a pH of 7.0 and a temperature of 30° C. Further, one unit of alkane or ammonium monooxygenase (AMO) or methane monooxygenase activity refers to the ability to convert 1 Lmol of ethylene to ethylene epoxide. Further, one unit of toluene dioxygenase refers to the ability to convert 1 Lmol of ethylene to ethylene epoxide. Assays for measuring nitrile hydratase activity, amidase activity, asparaginase activity, ACC deaminase activity, cyanoalanine synthase-like enzyme activity, alkane or ammonium monooxygenase (AMO) activity, methane monooxygenase activity, toluene dioxygenase (AMO-like) activity, and cyanidase activity are known in the art and include, for example, the detection of free ammonia. See, e.g., Fawcett and Scott, J. Clin. Pathol. 13:156-9 (1960).

Generally, any bacterial, fungal, plant, or animal cell capable of producing or being induced to produce nitrile hydratase, amidase, asparaginase, ACC deaminase activity, cyanoalanine synthase-like enzyme activity, alkane or ammonium monooxygenase (AMO) activity, methane monooxygenase activity, toluene dioxygenase activity, and cyanidase activity, or any combination thereof may be used herein. A nitrile hydratase, amidase, asparaginase, ACC deaminase, cyanoalanine synthase-like enzyme, alkane or ammonium monooxygenase, methane monooxygenase, toluene dioxygenase, and/or cyanidase may be produced constitutively in a cell from a particular organism (e.g., a bacterium, fungus, plant cell, or animal cell) or, alternatively, a cell may produce the desired enzyme or enzymes only following "induction" with a suitable inducing agent. "Constitutively" is intended to mean that at least one enzyme disclosed herein is continually produced or expressed in a particular cell type. Other cell types, however, may need to be "induced," as described above, to express nitrile hydratase, amidase, asparaginase, ACC deaminase, cyanoalanine synthase-like enzyme, alkane or ammonium monooxygenase, methane monooxygenase, toluene dioxygenase, and cyanidase at a sufficient quantity or enzymatic activity level to fungal growth. That is, an enzyme disclosed herein may only be produced (or produced at sufficient levels) following exposure to or treatment with a suitable inducing agent. Such inducing agents are known and outlined above. For example, the one or more bacteria are treated with an inducing agent such as urea, methyl carbamate, cobalt, asparagine, glutamine, or any mixture thereof, more particularly urea or methyl carbamate optionally in combination with asparagine or cobalt. Furthermore, as disclosed in U.S. Pat. Nos. 7,531,343 and 7,531,344, which are incorporated by reference in their entireties, entitled "Induction and Stabilization of Enzymatic Activity in Microorganisms," asparaginase I activity can be induced in *Rhodococcus rhodochrous* DAP 96622 (Gram-positive) or *Rhodococcus rhodochrous* DAP 96253 (Gram-positive), in medium supplemented with amide containing amino acids or derivatives thereof. Other strains of *Rhodococcus* can also preferentially be induced to exhibit asparaginase I enzymatic activity utilizing amide containing amino acids or derivatives thereof.

*P. chloroaphis* (ATCC Deposit No. 43051), which produces asparaginase I activity in the presence of asparagine and ACC deaminase, and *B. kletoglutamicum* (ATCC Deposit No. 21533), a Gram-positive bacterium that has also been shown to produce asparaginase activity, are also used in the disclosed methods. Fungal cells, such as those from the genus *Fusarium*, plant cells, and animal cells, that express a nitrile hydratase, amidase, and/or an asparaginase, may also be used herein, either as whole cells or as a source from which to isolate one or more of the above enzymes.

The nucleotide and amino acid sequences for several nitrile hydratases, amidases, and asparaginases (e.g., type I asparaginases) from various organisms are disclosed in publicly available sequence databases. A non-limiting list of representative nitrile hydratases and aliphatic amidases known in the art is set forth in Tables 1 and 2 and in the sequence listing. The "protein score" referred to in Tables 1 and 2 provide an overview of percentage confidence intervals (% Confid. Interval) of the identification of the isolated proteins based on mass spectroscopy data.

TABLE 1

Amino Acid Sequence Information for Representative Nitrile Hydratases

| Source organism | Accession No. | Sequence Identifier | Protein Score (% Confid. Interval) |
|---|---|---|---|
| *Rhodococcus* sp. | 806580 | SEQ ID NO: 1 | 100% |
| *Nocardia* sp. | 27261874 | SEQ ID NO: 2 | 100% |
| *Rhodococcus rhodochrous* | 49058 | SEQ ID NO: 3 | 100% |
| Uncultured bacterium (BD2); | 27657379 | SEQ ID NO: 4 | 100% |
| beta-subunit of nitrile hydratase *Rhodococcus* sp. | 806581 | SEQ ID NO: 5 | 100% |
| *Rhodococcus rhodochrous* | 581528 | SEQ ID NO: 6 | 100% |
| Uncultured bacterium (SP1); alpha-subunit of nitrile hydratase | 7657369 | SEQ ID NO: 7 | 100% |

TABLE 2

Amino Acid Sequence Information for Representative Aliphatic Amidases

| Source organism | Accession No. | Sequence Identifier | Protein Score (% Confid. Interval) |
|---|---|---|---|
| *Rhodococcus rhodochrous* | 62461692 | SEQ ID NO: 8 | 100% |
| *Nocardia farcinica* IFM 10152 | 54022723 | SEQ ID NO: 9 | 100% |

TABLE 2-continued

Amino Acid Sequence Information for Representative Aliphatic Amidases

| Source organism | Accession No. | Sequence Identifier | Protein Score (% Confid. Interval) |
|---|---|---|---|
| *Pseudomonas aeruginosa* PAO1 | 15598562 | SEQ ID NO: 10 | 98.3% |
| *Helicobacter pylori* J99 | 15611349 | SEQ ID NO: 11 | 99.6% |
| *Helicobacter pylori* 26695 | 2313392 | SEQ ID NO: 12 | 97.7% |
| *Pseudomonas aeruginosa* | 150980 | SEQ ID NO: 13 | 94% |

Optionally, host cells that have been genetically engineered to express a nitrile hydratase, amidase, asparaginase, ACC deaminase, cyanoalanine synthase-like enzyme, alkane monooxygenase, toluene dioxygenase, and/or cyanidase can be exposed to a location for inhibiting or reducing fungal growth or development of fungal growth. Specifically, a polynucleotide that encodes a nitrile hydratase, amidase, asparaginase, ACC deaminase, cyanoalanine synthase-like enzyme, alkane or ammonium monooxygenase, methane monooxygenase, toluene dioxygenase, or cyanidase (or multiple polynucleotides each of which encodes a nitrile hydratase, amidase, asparaginase, ACC deaminase, cyanoalanine synthase-like enzyme, alkane or ammonium monooxygenase, methane monooxygenase, toluene dioxygenase, or cyanidase) may be introduced by standard molecular biology techniques into a host cell to produce a transgenic cell that expresses one or more of the enzymes. The use of the terms "polynucleotide," "polynucleotide construct," "nucleotide," or "nucleotide construct" is not intended to limit to polynucleotides or nucleotides comprising DNA. Those of ordinary skill in the art will recognize that polynucleotides and nucleotides can comprise ribonucleotides and combinations of ribonucleotides and deoxyribonucleotides. Such deoxyribonucleotides and ribonucleotides include both naturally occurring molecules and synthetic analogues. The polynucleotides described herein encompass all forms of sequences including, but not limited to, single-stranded forms, double-stranded forms, and the like.

Variants and fragments of polynucleotides that encode polypeptides that retain the desired enzymatic activity (i.e., nitrile hydratase, amidase, asparaginase, ACC deaminase, cyanoalanine synthase-like enzyme, alkane or ammonium monooxygenase, methane monooxygenase, toluene dioxygenase, or cyanidase activity) may also be used herein. By "fragment" is intended a portion of the polynucleotide and hence also encodes a portion of the corresponding protein. Polynucleotides that are fragments of an enzyme nucleotide sequence generally comprise at least 10, 15, 20, 50, 75, 100, 150, 200, 250, 300, 350, 400, 450, 500, 550, 600, 650, 700, 800, 900, 1,000, 1,100, 1,200, 1,300, or 1,400 contiguous nucleotides, or up to the number of nucleotides present in a full-length enzyme polynucleotide sequence. A polynucleotide fragment will encode a polypeptide with a desired enzymatic activity and will generally encode at least 15, 25, 30, 50, 100, 150, 200, or 250 contiguous amino acids, or up to the total number of amino acids present in a full-length enzyme amino acid sequence. "Variant" is intended to mean substantially similar sequences. Generally, variants of a particular enzyme sequence will have at least 40%, 45%, 50%, 55%, 60%, 65%, 70%, 75%, 80%, 85%, 90%, 91%, 92%, 93%, 94%, 95%, 96%, 97%, 98%, 99% or more sequence identity to the reference enzyme sequence, as determined by standard sequence alignment programs. Variant polynucleotides described herein will encode polypeptides with the desired enzyme activity. By way of example, the relatedness between two polynucleotides or two polypeptides can be described as identity. The identity between two sequences can be determined using the Needleman-Wunsch algorithm (Needleman and Wunsch, 1970, *J. Mol. Biol.* 48:443-453) as implemented in the Needle program of the EMBOSS package (EMBOSS: The European Molecular Biology Open Software Suite, Rice et al., 2000, *Trends Genet.* 16:276-7). The output of Needle labeled "longest identity" is used as the percent identity and is calculated as (Identical Residues (i.e., nucleotides or peptides)×100)/(Length of Alignment−Total Number of Gaps in Alignment).

As used in the context of production of transgenic cells, the term "introducing" is intended to mean presenting to a host cell, particularly a microorganism such as *Escherichia coli*, with a polynucleotide that encodes a nitrile hydratase, amidase, asparaginase, ACC deaminase, cyanoalanine synthase-like enzyme, alkane or ammonium monooxygenase, methane monooxygenase, toluene dioxygenase, and/or cyanidase. Optionally, the polynucleotide will be presented in such a manner that the sequence gains access to the interior of a host cell, including its potential insertion into the genome of the host cell. The disclosed methods do not depend on a particular protocol for introducing a sequence into a host cell, only that the polynucleotide gains access to the interior of at least one host cell. Methods for introducing polynucleotides into host cells are well known, including, but not limited to, stable transfection methods, transient transfection methods, and virus-mediated methods. "Stable transfection" is intended to mean that the polynucleotide construct introduced into a host cell integrates into the genome of the host and is capable of being inherited by the progeny thereof. "Transient transfection" or "transient expression" is intended to mean that a polynucleotide is introduced into the host cell but does not integrate into the host's genome.

Furthermore, the nitrile hydratase, amidase, asparaginase, ACC deaminase, cyanoalanine synthase-like enzyme, alkane or ammonium monooxygenase, methane monooxygenase, toluene dioxygenase, or cyanidase nucleotide sequence may be contained in, for example, a plasmid for introduction into the host cell. Typical plasmids of interest include vectors having defined cloning sites, origins of replication, and selectable markers. The plasmid may further include transcription and translation initiation sequences and transcription and translation terminators. Plasmids can also include generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or optimally both. For general descriptions of cloning, packaging, and expression systems and methods, see Giliman and Smith, Gene 8:81-97 (1979); Roberts et al., *Nature* 328:731-734 (1987); Berger and Kimmel, Guide to Molecular Cloning Techniques, Methods in Enzymology, Vol. 152 (Academic Press, Inc., San Diego, Calif.) (1989); Sambrook et al., Molecular Cloning: A Laboratory Manual, Vols. 1-3 (2d ed; Cold Spring Harbor Laboratory Press, Plainview, N.Y.) (1989); and Ausubel et al., Current Protocols in Molecular Biology, Current Protocols (Greene Publishing Associates, Inc., and John Wiley & Sons, Inc., New York; 1994 Supplement) (1994). Transgenic host cells that express one or more of the enzymes may be used in the disclosed methods as whole cells or as a biological source from which one or more enzymes can be isolated.

Apparatuses and carriers for inhibiting or reducing fungal growth and for performing the methods disclosed are further provided. In particular embodiments, an apparatus or carrier for inhibiting or reducing fungal growth comprising a catalyst that comprises one or more bacteria selected from the group consisting of *Rhodococcus* spp., *Pseudomonas chloroaphis, Brevibacterium ketoglutamicum*, and mixtures thereof is disclosed herein. *Rhodococcus rhodochrous* DAP 96253 strain, *Rhodococcus rhodochrous* DAP 96622 strain, *Rhodococcus erythropolis*, or mixtures thereof may be used in certain aspects. The one or more bacteria of an apparatus or carrier are provided in a quantity sufficient to inhibit or reduce fungal growth as defined herein above. In other aspects, the catalyst comprises one or more enzymes (i.e., nitrile hydratase, amidase, asparaginase, ACC deaminase, cyanoalanine synthase-like enzyme, alkane or ammonium monooxygenase, methane monooxygenase, toluene dioxygenase, and/or cyanidase) in a quantity or at an enzymatic activity level sufficient to inhibit or reduce fungal growth. Sources of the desired enzymes for use as a catalyst in the apparatuses or carriers disclosed herein are also described in detail above. For example, the catalyst may be used in the form of whole cells that produce (or are induced or genetically modified to produce) one or more of the enzymes or may comprise the enzyme(s) themselves in an isolated, purified, or semi-purified form. A carrier for compositions for inhibiting or reducing fungal growth can, for example, be selected from the group consisting of paper, DEAE, cellulose, waxes, glutaraldehyde, and granular activated carbon.

Apparatuses for inhibiting or reducing fungal growth encompassed by the present disclosure may be provided in a variety of suitable formats and may be appropriate for single use or multiple uses (e.g., "re-chargeable"). Furthermore, the apparatuses or carriers find use in both residential and commercial settings. For example, such apparatuses or carriers can be integrated into residential or commercial refrigerators, showers, or any place an undesirable fungus may grow. Exemplary, non-limiting apparatuses are described herein below and depicted in FIGS. 5-8.

In particular embodiments, the catalyst is provided in an immobilized format. Any process or matrix for immobilizing the catalyst may be used so long as the ability of the one or more bacteria (or enzymes) to inhibit or reduce fungal growth is retained. For example, the catalyst may be immobilized in a matrix comprising alginate (e.g., calcium alginate), carrageenan, DEAE-cellulose, or polyacrylamide. Other such matrices are well known in the art and may be further cross-linked with any appropriate cross-linking agent, including but not limited to glutaraldehyde and/or polyethylenimine, to increase the mechanical strength of the catalyst matrix. In one aspect, the catalyst is immobilized in a glutaraldehyde cross-linked DEAE-cellulose matrix. The catalyst, particularly the catalyst in an immobilized form, may be further presented as a "catalyst module element." A catalyst module element comprises a catalyst, such as an immobilized catalyst, within an additional structure that, for example, reduces potential contact with the catalyst, facilitates replacement of the catalyst, or permits air flow across the catalyst.

In one embodiment, the matrix comprises alginate, or salts thereof. Alginate is a linear copolymer with homopolymeric blocks of (1-4)-linked ß-D-mannuronate (M) and its C-5 epimer α-L-guluronate (G) residues, respectively, covalently linked together in different sequences or blocks. The monomers can appear in homopolymeric blocks of consecutive G-residues (G-blocks), consecutive M-residues (M-blocks), alternating M and G-residues (MG-blocks), or randomly organized blocks. In one embodiment, calcium alginate is used as the substrate, more particularly calcium alginate that has been cross-linked, such as with polyethylenimine, to form a hardened calcium alginate substrate. Further description of such immobilization techniques can be found in Bucke (1987) "Cell Immobilization in Calcium Alginate" in *Methods in Enzymology*, Vol. 135(B) (Academic Press, Inc., San Diego, Calif.; Mosbach, ed.), which is incorporated herein by reference. An exemplary method of immobilization using polyethylenimine cross-linked calcium alginate is also described below in Example 5. In another embodiment, the matrix comprises an amide-containing polymer. Any polymer comprising one or more amide groups could be used. In one embodiment, the substrate comprises a polyacrylamide polymer.

Increased mechanical strength of an immobilized catalyst matrix can be achieved through cross-linking. For example, cells can be chemically cross-linked to form agglutinations of cells. In one embodiment, cells harvested are cross-linked using glutaraldehyde. For example, cells can be suspended in a mixture of de-ionized water and glutaraldehyde followed by addition of polyethylenimine (PEI) until maximum flocculation is achieved. The cross-linked cells (typically in the form of particles formed of a number of cells) can be harvested by simple filtration. Further description of such techniques is provided in Lopez-Gallego et al. (2005) *J. Biotechnol.* 119:70-75, which is hereby incorporated by reference in its entirety.

In certain aspects, the immobilized catalyst or one or more catalyst module elements are placed in, placed on, or affixed to a "physical structure." The physical structure includes but is not limited to a film, sheet, coating layer, box, pouch, bag, or slotted chamber capable of holding one or more catalyst module elements. In certain embodiments, the physical structure comprises a container suitable for transport or storage of fruit, vegetables, or flowers. The physical structure may further comprise more than one individual structure, whereby all of the individual structures are connected to a central catalyst or catalyst module element. A physical structure described herein above may optionally be refrigerated by external means or comprise a refrigeration unit within the physical structure itself. By way of example, the physical structure can be a sheet or film comprising a sufficient quantity of the one or more bacteria, one or more enzymes, or enzymatic extract necessary to inhibit or reduce fungal growth. Optionally, the sheet or film is pullulan, or cellophane. Such sheets or films can be used to wrap the plant or plant part. By way of example, the film can be made of pullulan and used to wrap flowers. In certain embodiments, the physical structure comprises or is a container suitable for transport or storage of grain, e.g., a grain silo.

Figure 5:
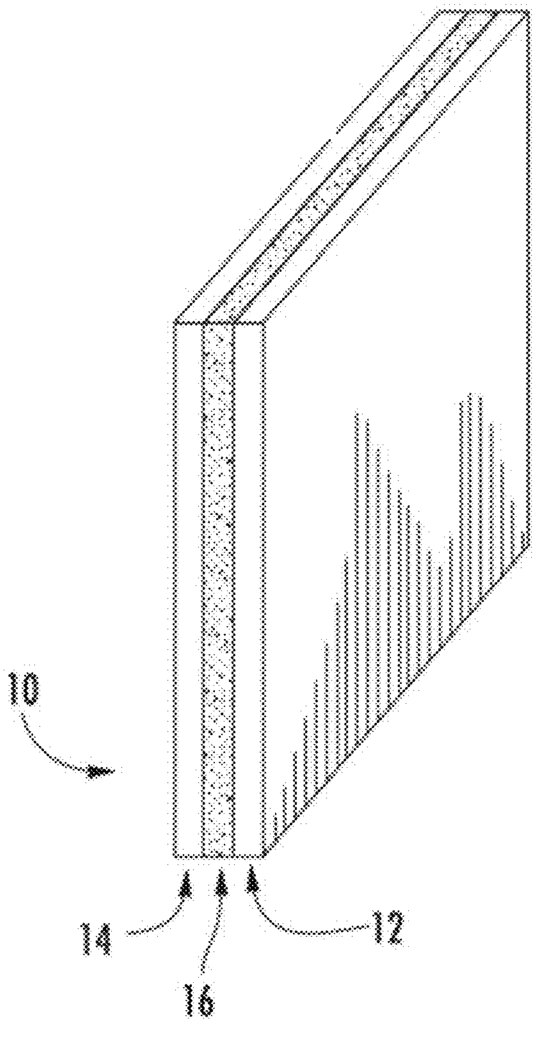
FIG. 5 shows a non-limiting depiction of a three-layer apparatus for inhibiting or delaying fungal growth. The outer layers provide structural integrity to the apparatus. The catalyst layer, as defined herein below, comprises one or more of the enzymes or one or more bacteria disclosed herein and is located between the outer layers.

In particular embodiments, air-permeable catalyst apparatuses for inhibiting or reducing fungal growth comprising multiple layers are provided. For example, as shown in FIG. 5, a catalyst apparatus 10 can include outer layers 12 and 14 and an intermediate catalyst layer 16 located between the outer layers 12 and 14. The catalyst layer 16 comprises one or more bacteria (e.g., *Rhodococcus* spp., *Pseudomonas chloroaphis, Brevibacterium ketoglutamicum*, and mixtures thereof) or enzymes (a nitrile hydratase, amidase, asparaginase, ACC deaminase, cyanoalanine synthase-like enzyme, alkane or ammonium monooxygenase, methane monooxygenase, toluene dioxygenase, cyanidase, and mixtures thereof), wherein the one or more bacteria or enzymes are provided in a quantity sufficient to inhibit or reduce fungal growth, and a third layer. In this embodiment, one or more of the outer layers 12 and 14 provide structural integrity to the catalyst apparatus 10. The outer layers 12 and 14 typically permit air flow to the catalyst layer 16 although, in some embodiments, it may be advantageous to have an outer layer that is not air-permeable, e.g., if apparatus forms the side of the box and there is a desire not to allow the outermost layer of the box to expose the catalyst layer to the environment. The catalyst apparatus 10 can be provided in reusable or non-reusable bags or pouches. In one embodiment, the catalyst layer 16 comprises *Rhodococcus* spp. cells, particularly *Rhodococcus rhodochrous* DAP 96253 strain, *Rhodococcus rhodochrous* DAP 96622 strain, *Rhodococcus erythropolis*, or mixtures thereof. Bacterial cells utilized as a catalyst in an apparatus disclosed herein may be induced with one or more inducing agents (e.g., urea, methyl carbamate, cobalt, asparagine, glutamine, or a mixture thereof), as described in detail above.

Figure 6A:
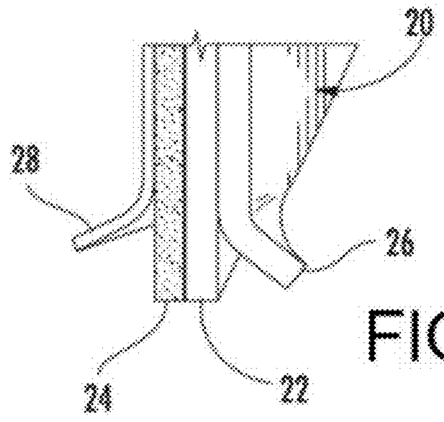
FIGS. 6A to 6C provide non-limiting depictions of various apparatuses for inhibiting or delaying fungal growth. These apparatuses comprise a catalyst layer, one or more layers intended to provide structural integrity, and one or more layers intended to be removed prior to use of the apparatus. Removal of one or more of these layers may, for example, expose an adhesive for attachment of the apparatus to another physical structure.
Figure 6B:
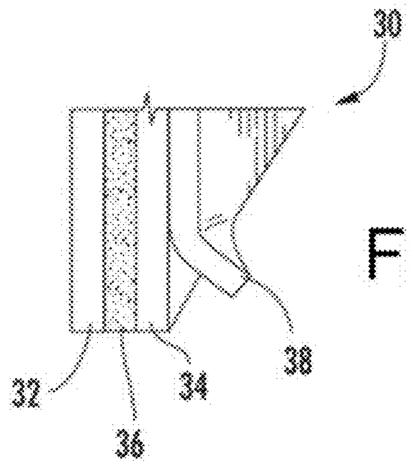
Figure 6C:
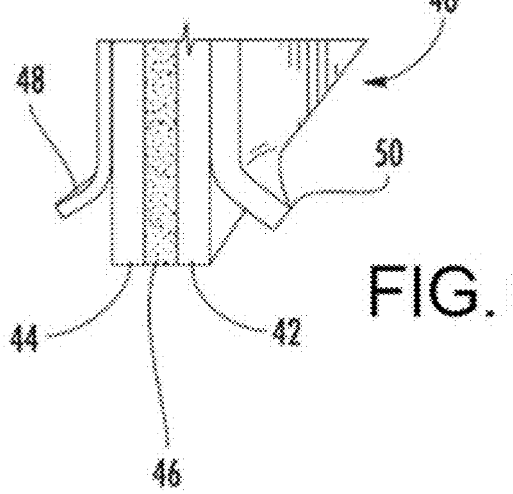

FIG. 6 illustrates alternative apparatuses for inhibiting or reducing fungal growth. These apparatuses comprise multiple layers, wherein one or more of the layers are removable. As shown in FIG. 6, top diagram, the apparatus can include an air-permeable structural layer 22 and a catalyst layer 24. Removable layers 26 and/or 28 can be provided along the structural layer 22 and/or the catalyst layer 24 and are typically intended to be removed prior to using or activating the catalyst. In certain aspects, the removal of the removable layers 26 and 28 expose an adhesive that facilitates placement or attachment of the catalyst structure to a separate physical structure. FIG. 6, middle diagram, illustrates an alternative embodiment wherein the apparatus 30 includes two air-permeable structural layers 32 and 34, an intermediate catalyst layer 36 and a removable layer 38. FIG. 6, bottom diagram, illustrates yet another embodiment wherein the apparatus 40 includes two air-permeable structural layers 42 and 44, an intermediate catalyst layer 46 and two removable layers 48 and 50.

Figure 7A:
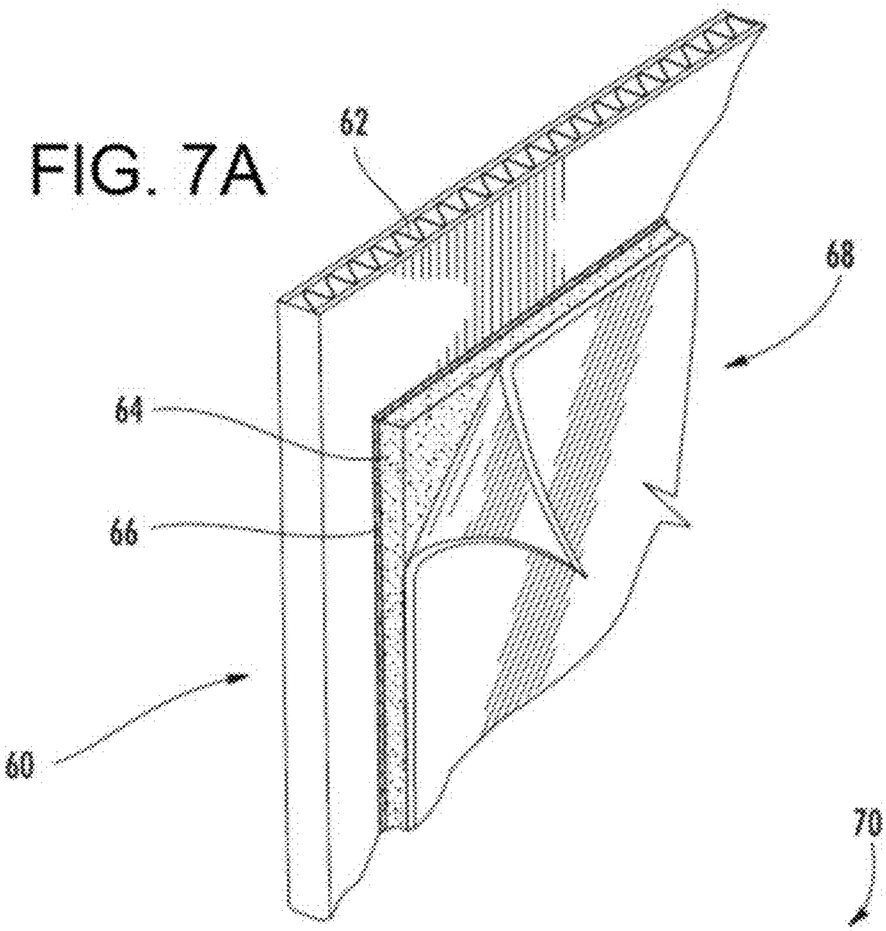
FIGS. 7A and 7B show non-limiting depictions of an apparatus for inhibiting or delaying fungal growth. The apparatus comprises a catalyst immobilized on a layer of film and attached to a physical structure (e.g., a box suitable for storage/transportation of fruit).
Figure 7B:
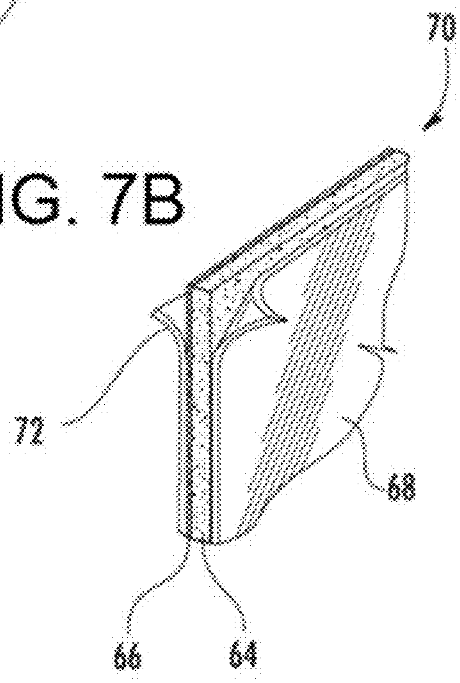

FIG. 7 illustrates an alternative embodiment 60 wherein the catalyst is affixed to the interior of a container such as a cardboard box. As shown in FIG. 7, top diagram, a side 62 of the container includes a catalyst layer 64 attached thereto through the use of an adhesive layer 66. A peelable film 68 can be provided adjacent the catalyst layer 64 to protect the catalyst layer from exposure to the environment. The peelable film 68 can be removed to activate the catalyst in the catalyst layer 64 by exposing the catalyst to an object provided in the container to thereby inhibit or reduce fungal growth.

FIG. 7, bottom diagram, illustrates a catalyst structure 70 prior to affixing the catalyst structure to a container interior in the manner shown in FIG. 7, bottom diagram. In addition to the catalyst layer 64, the adhesive layer 66, and the peelable film 68, the catalyst structure 70 includes an additional peelable film 72. The peelable film 72, like the peelable film 68, protects the catalyst structure 70 when it is packaged, shipped or stored. The peelable film 72 can be removed to expose the adhesive layer 66 to allow the catalyst structure 70 to be affixed to the container interior in the manner illustrated in FIG. 7A.

Figure 8:
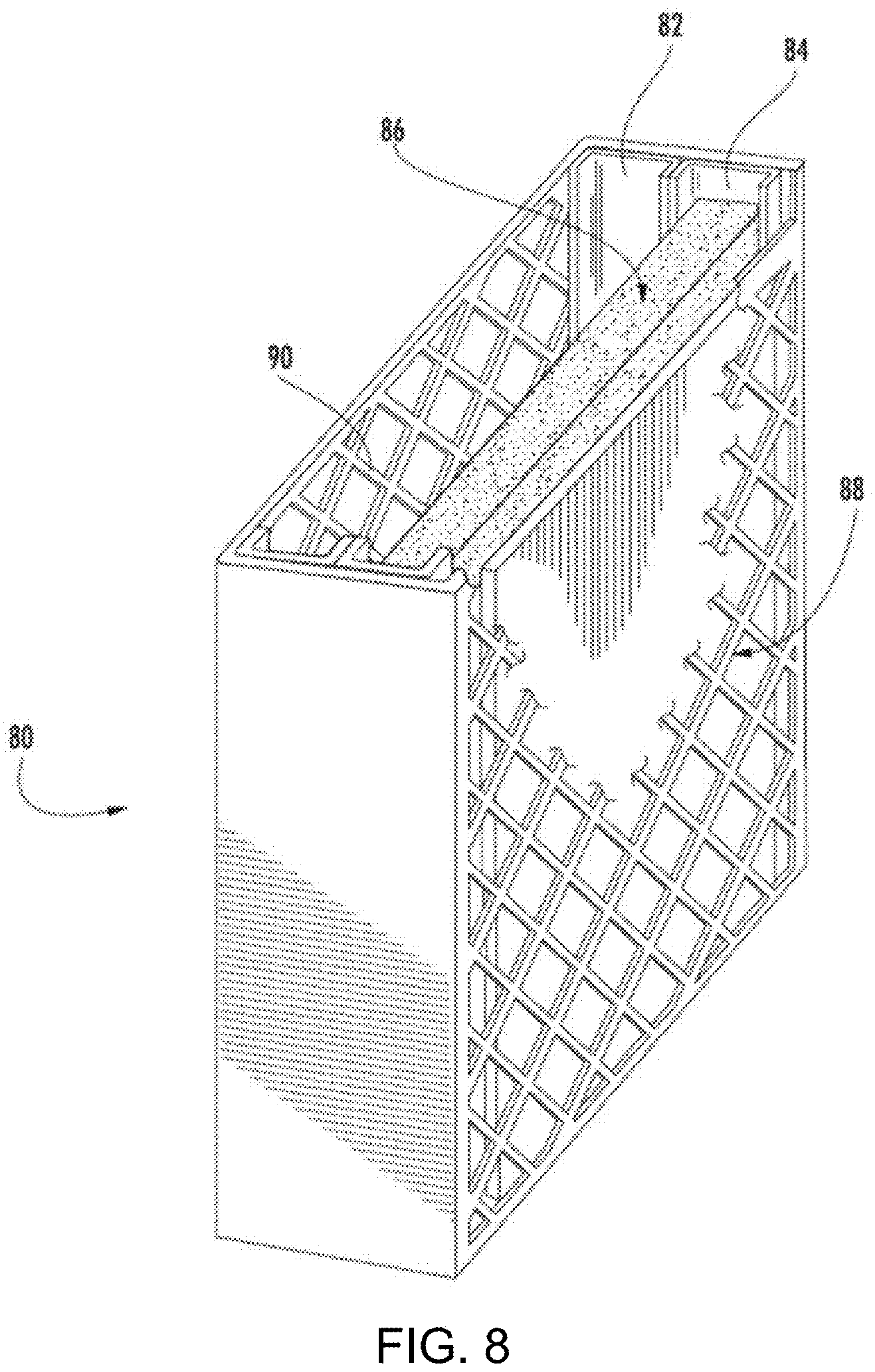
FIG. 8 provides a non-limiting depiction of an apparatus for inhibiting or delaying fungal growth. The apparatus comprises a slotted chamber structure that permits the insertion and replacement of one or more catalyst module elements, as defined below. The outer layers of the physical structure may be composed of a material that permits air to flow into the catalyst.

FIG. 8 illustrates a catalyst structure 80 that includes two slots 82 and 84 for receiving a catalyst module (e.g. module 86). The catalyst module 86 is air-permeable and can be easily inserted into or removed from slot 84. Thus, the catalyst module 86 can be readily replaced if a new catalyst module is desired for use in the catalyst structure 80. The catalyst module 86 includes a catalyst such as described herein and that is preferably immobilized in a matrix. The catalyst structure 80 can include opposed air-permeable surfaces 88 and 90 such as mesh screens to allow air flow through the catalyst module 86. The catalyst structure 80 can, in alternative embodiments, include only one air-permeable surface, two non-opposed air-permeable surfaces or more than two air-permeable surfaces as would be understood to one of skill in the art. Although FIG. 8 includes two slots 82 and 84 for receiving a catalyst module (e.g. module 86), it would be understood to one of skill in the art that the catalyst structure 80 could include one or more slots for receiving a module. The catalyst structure 80 can be provided within a container used to transport an object or can be affixed to a container, e.g., through the use of an adhesive layer as discussed herein.

The skilled artisan will further recognize that any of the methods, apparatuses, physical structures, compositions, or carriers disclosed herein can be combined with other known methods, apparatuses, physical structures, compositions, and carriers for inhibiting or reducing fungal growth. Moreover, as described above, increased ethylene production has also been observed during attack of plants or plant parts by pathogenic organisms. Accordingly, the methods and apparatuses disclosed herein may find further use in improving plant response to pathogens.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Example 1: Inhibition of *Cladosporium* Fungal Infection

Figure 1B:

The images shown in FIG. 1 are typical for all experiments comprising exposure of the induced catalyst to peaches. The experiments were conducted on peaches that had gone through a process of hydro-cooling, washing, and application of wax and fungicide. The peaches treated with the induced catalyst were free of visible mold growth, whereas the fungicide treated peaches showed significant mold growth (FIG. 1). All peaches (processed and non-processed) were first placed into groups of similar peaches (size, color, general appearance, and free of blemishes/wounds) and then randomized into control (processed peaches) and experimental (exposed to catalyst made from induced cells) sub-groups. Thus, both control and experimental sub-groups contained similar peaches. Therefore, the appearance of mold on the control peaches was not due to the process of selecting samples for the control and experimental groups.

The experiments with peaches were also confirmed with bananas. In these experiments, mold was noted in fungicide treated bananas, but not bananas treated with induced *Rhodococcus* cells. The mold was especially noted where the banana fingers/hands were broken off from larger hands of bananas.

To confirm the results of the experiments with the peaches and bananas, experiments were designed to use spores harvested from *Cladosporium* sp., a mold commonly isolated from the peaches. Spore suspensions containing a defined number of spores were seeded onto filter membranes (0.2 u) and then placed on different media both in the presence and absence of *Rhodococcus* cells. The media employed were selected for: a) good mold growth, good growth of *Rhodococcus* with low or no catalyst activity, and c) good growth of *Rhodococcus* with induced catalyst activity to investigate the effect of *Rhodococcus* cells grown on media containing different levels of induction on the sporulation of *Cladosporium.*

*Rhodococcus* sp DAP 96253 cultures were started from glycerol stocks stored at minus 80° C. by transferring 1 ml of the glycerol stock to 250 ml nutrient broth. The culture was incubated at 30° C. while shaking at 150 rpm for 2 days. Nutrient agar plates were inoculated and incubated for 2 days at 30° C.; cells from these plates were scrapped and used as an inoculum for YEMEA plates supplemented with glucose and the following additives: cobalt, urea, and asparagine. The YEMEA plates were incubated for a week at 30° C. *Cladosporium* sp. was streaked on SAB plates and grown for 7 days. The spores were harvested according to protocol and $10^3$ spores were transferred to membranes. The membranes were placed over a lawn of *Rhodococcus* cells grown on media with different supplements, and data was collected after 12 days.

It was shown that the fully induced *Rhodococcus* cells promote the inhibition of spore germination and mycelia development in the *Cladosporium* sp. spores (FIG. 2). Additional experiments were conducted using spores from other molds isolated from the peaches, and these experiments provided similar results.

From these experiments it was clear that the *Rhodococcus* cells inhibited the sporulation of *Cladosporium* regardless of supplements used in growth media provided that the *Rhodococcus* cells were induced, however the most significant inhibition was observed when *Rhodococcus rhodochrous* DAP 96253 was grown on induction media that showed high levels of delayed ripening in fruit.

Experiments were conducted to determine if physical contact between the catalyst and the fungi were necessary for fungal inhibition.

*Rhodococcus* rhodochrous DAP 96253 cultures were started from glycerol stocks stored at −80° C. by transferring 1 ml of the glycerol stock to 250 ml nutrient broth. Cultures were incubated at 30° C. while shaking at 150 rpm for 2 days. Nutrient agar plates were inoculated and incubated for 2 days at 30° C.

*Fusarium* sp isolated from the peaches was streaked on SAB plates and grown for 7 days. The spores were harvested and diluted to $10^3$ spores/ml (in phosphate buffer).

Compartmentalized Petri dishes (3 or 4 sections per plate) were. At least one section contained medium (YEMEA) suitable for the growth of *Rhodococcus*. The other two sections contained medium (SAB) suitable for the outgrowth of *Fusarium* spores and for growth of the *Fusaraium*. The YEMEA section(s) were inoculated with *Rhodococcus* cells, and then incubated for a week at 30° C. until a lawn of *Rhodococcus* covered the YEMEA section(s). A 50 LI aliquot of *Fusarium* spore suspension was then transferred to the SAB sections of the plate. The plates were incubated for an additional three days at 30° C.

*Rhodococcus* cells were also scrapped from YEMEA (8 plates) that contained different supplements such as urea, cobalt chloride, asparagine and suspended in 10 ml phosphate buffer. The cell suspension was transferred to a section in a compartmentalized Petri dish containing no media. A membrane containing *Fusarium* sp spores ($10^3$ spores/ml) was transferred to the section of the plate containing SAB (Sabouraud's Dextrose Agar, a medium which permits abundant growth of the *Fusarium* sp.) media.

Figures 3A, 3B, 3C, 3D:
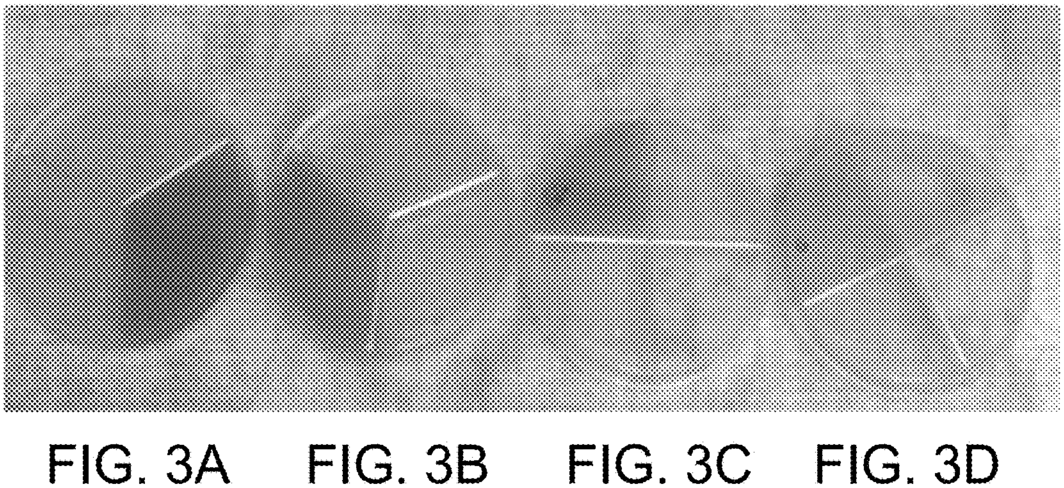
FIGS. 3A to 3D show fungal inhibition after exposure to *Rhodococcus* for 6 days. Sectored plates were used such that media supporting *Rhodococcus* growth were used in selected sectors while media supporting fungal growth was placed in the other sectors.
Figures 4A, 4B, 4C, 4D:
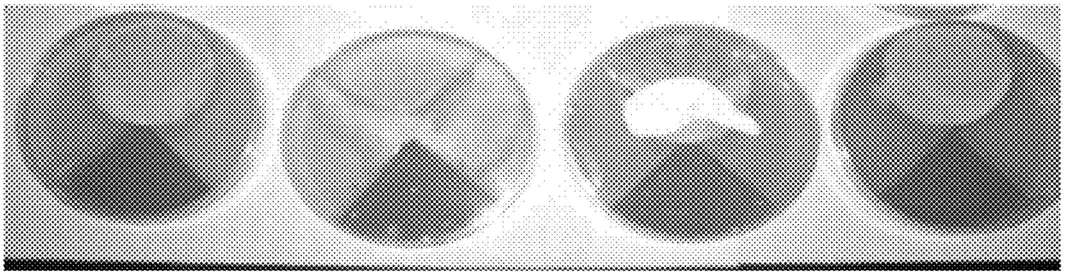
FIGS. 4A to 4D show the effect of *Rhodococcus* cells on *Fusarium* sp. sporulation.

The images provided in FIG. 3 demonstrated that induced cells of *Rhodococcus* do not need to be in contact with the fungal spores to inhibit spore germination and subsequent growth of the fungus. This figure also shows that non-induced cells have no impact on spore germination and subsequent growth. FIG. 4 shows that cells of *Rhodococcus* when removed from growth medium and placed in buffer still inhibited germination and growth of fungus (*Fusarium* sp.) provided the growth medium from which the cells were taken was a media that would induce the *Rhodococcus* cells. Non-induced cells had no effect on spore germination and subsequent growth. The results show that once induced, the *Rhodococcus* cells retain the ability to inhibit fungal spore germination and subsequent growth.

These experiments demonstrated that the *Rhodococcus* catalyst does not have to be in physical contact for fungal inhibition to occur. Inhibition of fungal spore germination and mold growth was seen in all of the fungal isolates obtained from the peaches.

Experiments were also conducted to determine whether the catalyst needs to be freshly prepared in order to inhibit fungal growth. Glutaraldehyde/PEI immobilized, induced cells of *Rhodococcus rhodochrous* DAP 96253 exhibit the ability to inhibit fungal growth on fruit whether the catalyst was freshly prepared or has been stored for some time. The catalyst was stored at −80° C., −20° C., 4° C. and room temperature. Catalyst stored at room temperature for four weeks was still capable of inhibiting fungal growth.

To determine if the catalyst was capable of inhibiting fungal growth in the absence of fruit and/or plant matter, induced *Rhodococcus rhodochrous* DAP 96253 cells were exposed to a fungus. It was noted that the longer the induced cells were exposed to the fungus, the greater the effect on inhibiting fungal growth was observed. For example, if the fungi were exposed for only 48 hours, some recovery of fungus is observed. However, exposure of the catalyst to the fungus for 96 hours results in no recovery of the fungus.

It was observed during the experiments that methyl carbamate was capable of inducing the *Rhodococcus rhodochrous* DAP 96253 cells for inhibiting fungal growth. The concentration range of the methyl carbamate was essentially the same as that for urea in inducing the *Rhodococcus* cells.

Further, it was observed during the experiments that live, induced *Rhodococcus rhodochrous* DAP 96253 cells placed in proximity of uninduced cells (e.g., uninduced *Rhodococcus rhodochrous* DAP 96253, *Rhodococcus rhodochrous* DAP 96622, or *Rhodococcus erythropolis* ATCC 47072 cells) were capable of inducing the uninduced cells to inhibit fungal growth.

Inhibition of fungal growth was observed for other spores, including *Aspergillus niger* and *G. destructans.*

Example 2: Inhibition of Spore Germination in Spores of *Geomyces destructans*

The psychrophilic fungus, *Geomyces destructans*, is the causative agent of "White Nose Syndrome" in bats, a disease which affects the bats during hibernation. To date, more than 4 million bats have died from this disease, which has had a significant negative impact on natural pollination.

Figure 9:
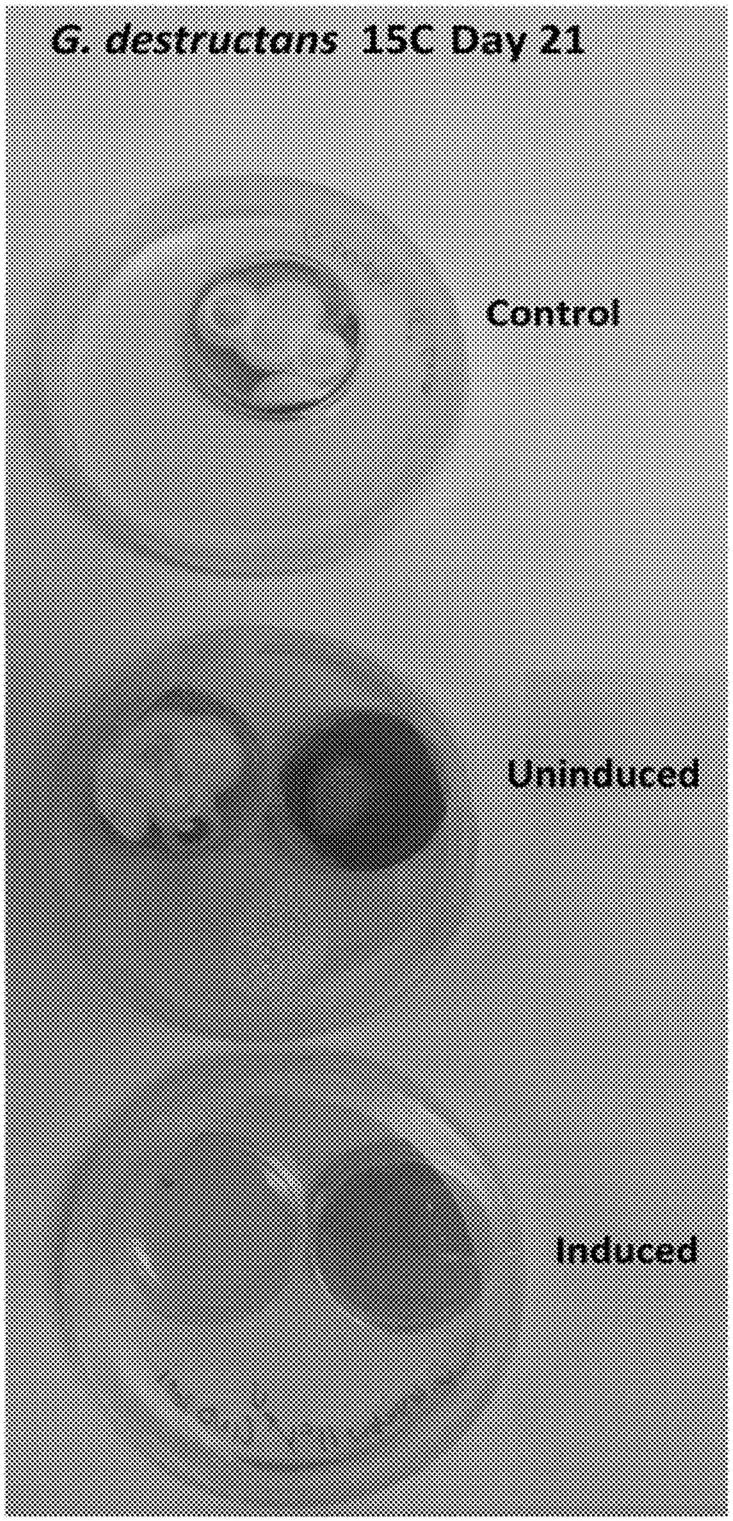
FIG. 9 is a comparison of Control Germination and Growth of *G. destructans* Spores, with Spores Exposed to Non-Induced and to Induced Cells of *R. rhodochrous* DAP 96253, at 15° C.

The optimum temperature for growth of *G. destructans* is 15° C., and growth will occur at 4° C. Control plates of SDA (Sabouraud's Dextrose Agar) showed abundant mycelia growth and conidiation at 15° C., and slower growth and conidiation at 4° C. Uninduced cells of *Rhodococcus rhodochrous* DAP 96253 (grown at 30° C. and then placed in proximity to the *G. destructans*) had no effect on the germination, growth, and spore formation of *G. destructans* spores placed on SDA at either 15° or 4° C. (FIG. 9). However, when induced cells of *R. rhodochrous* DAP 96253 were placed in proximity to the *G. destructans* spores, at 15° C., no germination of the *G. destructans* spores was detected. The induced cells, of *R. rhodochrous* DAP 96253, continue to show efficacy against *G. destructans* germination after 41 days (current maximum duration of the experiment).

Figure 10:
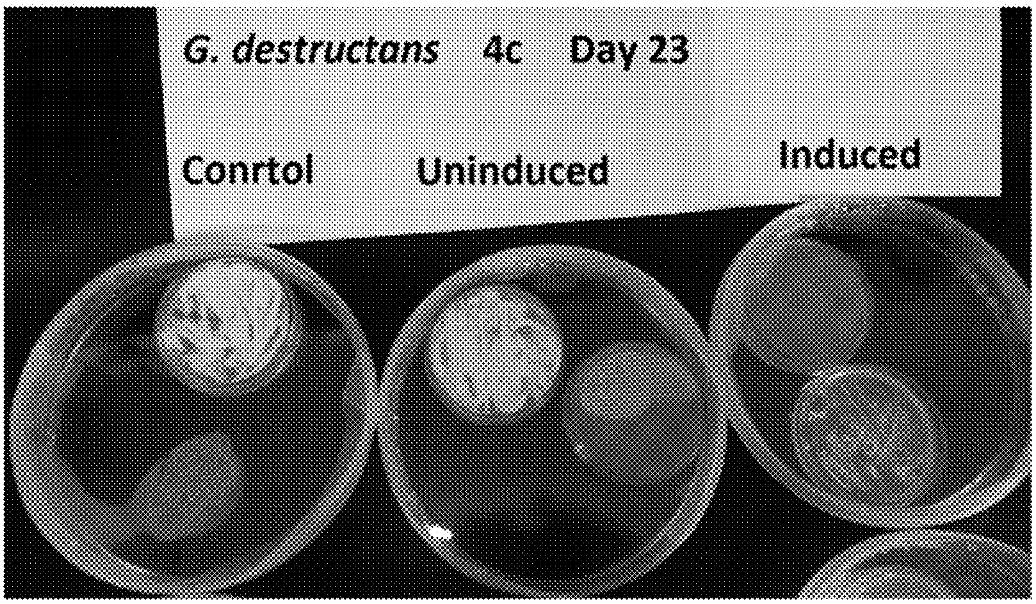
FIG. 10 is a comparison of Control Germination and Growth of *G. destructans* Spores, with Spores Exposed to Non-Induced and to Induced Cells of *R. rhodochrous* DAP 96253, at 4° C.
Figure 11:
FIG. 11 shows Control Peaches stored at 4° C. for 3 weeks.
Figure 12:
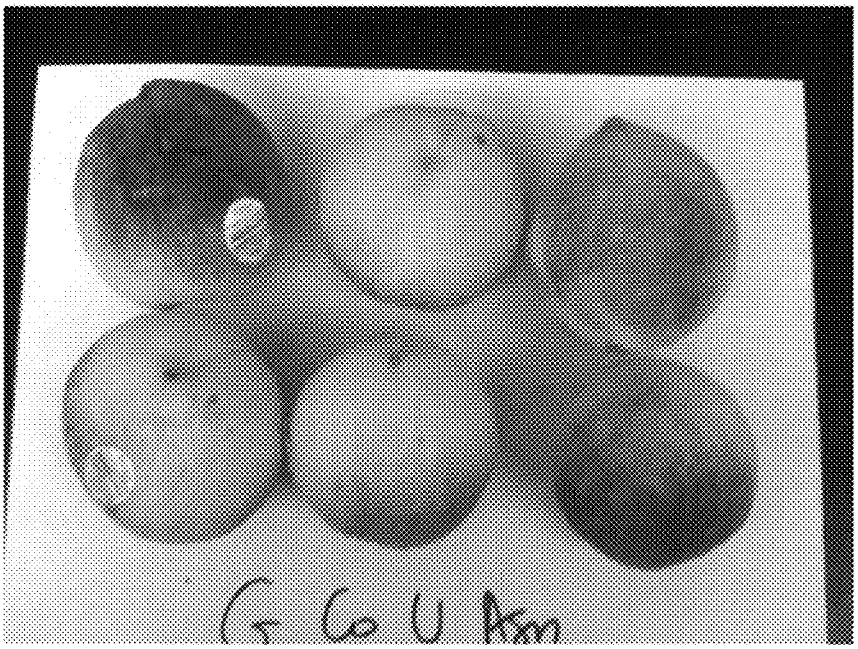
FIG. 12 shows fruits were stored at 4° C. for 3 weeks, then exposed to *Rhodococcal* catalyst for 7 days. *Rhodococcal* cells were grown on media with cobalt, urea and asparagine.
Figure 13:
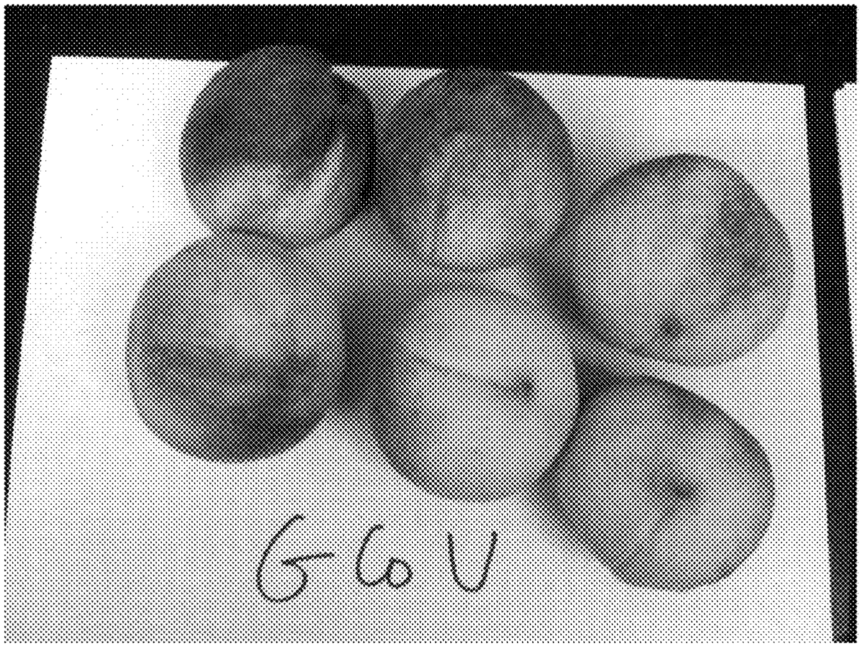
FIG. 13 shows fruits stored at 4° C. for 3 weeks, and then exposed to *Rhodococcal* catalyst for 7 days. *Rhodococcal* cells were grown on media with cobalt and urea.
Figure 14:
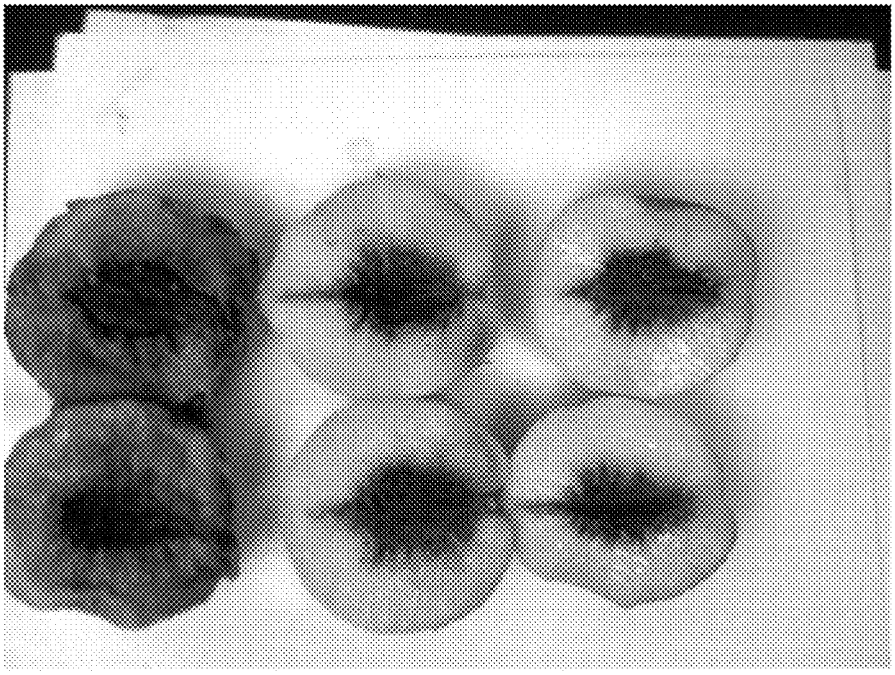
FIG. 14 shows fruits stored at 4° C. for 3 weeks, and then exposed to *rhodococcal* catalyst for 7 days. A—Control showing chill injury, B—exposed to cells induced with cobalt and urea, C—exposed to cells induced with cobalt, urea and asparagine.
Figure 15:
FIG. 15 shows untreated Control Peaches, held at 6.1° C. for 7 days then placed at room temperature for 3 days.
Figure 16:
FIG. 16 shows Control Peaches treated with Commercial Fungicide, held at 6.1° C. for 7 days then placed at room temperature for 3 days.
Figure 17:
FIG. 17 shows peaches placed in Proximity to Catalyst, held at 6.1° C. for 7 days then placed at room temperature for 3 days.
Figure 18:
FIG. 18 shows peaches treated with Commercial Fungicide and placed in proximity to catalyst, held at 6.1° C. for 7 days then placed at room temperature for 3 days.

At 4° C., reduced germination, and abnormal mycelia formation were noted for *G. destructans* spores exposed to induced cells of *R. rhodochrous* DAP 96253 (FIG. 10). At 7° C., reduced growth is noted.

It is noted that when the *G. destructans* spores (on SDA at 15° C.) are exposed to induced cells of *R. rhodochrous* DAP 96253, for several days, and the *R. rhodochrous* DAP 96253 cells are then removed, the *G. destructans* spores fail to germinate at all. This suggests that the inhibition exhibited at 15° C. is fatal for the *G. destructans* spores.

If the experiments conducted at 15° C. are repeated using a much larger container (1.1 gallon), complete inhibition is still noted.

Example 3: Effect of Low Temperature on the Activity of Selected Enzymes in Induced Cells of *Rhodococcus rhodochrous* DAP 96253 in Different Storage Buffers The effect of low temperature on the activity of selected enzymes in induced cells of *Rhodococcus rhodochrous* DAP 96253 was evaluated in Different Storage Buffers. The results are shown in Table 3.

TABLE 3

Comparison of Selected Enzyme Activities for Induced Cells Held at 4° C. and at 25° C. in Various Buffers.

| | | NHase (units/mg cdw) | | | | Amidase (units/mg cdw) | | | | B Cyanoalanine synthase like (units/mg cdw) | | | | Cyanidase (units/mg cdw) | | | |
|---|---|---|---|---|---|---|---|---|---|---|---|---|---|---|---|---|---|
| ° C. | Buffer/ | 7 d | 14 d | 21 d | 28 d | 7 d | 14 | 21 d | 28 d | 7 d | 14 d | 21 d | 28 d | 7 d | 14 d | 21 d | 28 d |
| 4 | M9 | 150 | 255 | 85 | 182 | 8 | 6 | 12 | 5 | 5 | 6 | 5 | 5 | 2 | 3 | 2 | 1 |
| | PB + Tre | 165 | 213 | 201 | 208 | 7 | 5 | 6 | 4 | 4 | 4 | 4 | 6 | 3 | 1 | 2 | 1 |
| | Cell Paste (no buffer) | 174 | 241 | 75 | 284 | 17 | 17 | 8 | 11 | 4 | 6 | 6 | 8 | 1 | 13 | 10 | 7 |
| RT | M9 | 124 | 203 | 151 | 188 | 4 | 5 | 4 | 3 | 5 | 5 | 5 | 4 | 8 | 1 | 2 | 1 |
| | PB + Tre | 140 | 235 | 220 | 273 | 3 | 4 | 3 | 3 | 5 | 5 | 4 | 4 | 2 | 1 | 1 | 1 |
| | Cell Paste (no buffer | 135 | 215 | 97 | 314 | 15 | 12 | 9 | 8 | 5 | 6 | 6 | 5 | 13 | 17 | 13 | 7 |
| | Initial Activity | 220 | | | | 10 | | | | 8 | | | | 9 | | | |

Example 4: Effect on Peaches Stored at 4-7° C. for Three Weeks

Procedures

*Rhodococcus* sp DAP 96253 cultures were started from glycerol stocks stored at −80° C. by transferring 1 ml of the glycerol stock to 250 ml nutrient broth. The culture was incubated at 30° C. while shaking at 150 rpm for 2 days. Nutrient agar plates were inoculated and incubated for 2 days at 30° C.; cells from these plates were scrapped and used as an inoculum for YEMEA plates supplemented with glucose and the following additives: cobalt, urea, and asparagine. The YEMEA plates were incubated for a week at 30° C. The cells were scrapped from the YEMEA plates and weighed (5-10 g), a sample of the cells was taken and Nitrile Hydratase (NHase) Amidase and ACC deaminase activities determined. Results are shown in Table 4.

*Rhodococcal* cells (5 g-10 g) were suspended in 10 ml 50 mM phosphate buffer and transferred to a Petri dish which was placed in a brown paper bag containing 6 peaches that had been stored at 4° C. for 3 weeks. The bags were closed and left at room temperature for 7 days. This experiment was repeated three times

Carbohydrate Determination 10 g samples of peaches (3) were taken after exposure and transferred to 10 ml water in 50 ml tube. The samples were crushed on ice and centrifuged for 10 mins at 4,000 rpm, 1 ml samples were taken and transferred to microcentrifuge tubes and centrifuged for 10 min at 13,000 rpm. Samples were diluted 1:100 followed by 1:10.

Glucose stock solution was prepared (1 mg/ml), a standard solution of 100 ug/ml was prepared from the stock and used as a standard.

Anthrone reaction was carried out on the samples, standard and negative control in glass test tubes by adding 5 ml of anthrone reagent (200 mg anthrone dissolved in 100 ml 75% sulfuric acid) to 1 ml of sample, the solution was mixed and placed in a water bath at 100° C. for 3.5 mins. The tubes were allowed to cool and absorbance read at 625 nm. Results are shown in Table 5.

TABLE 4

Selected Enzyme Activities of the Induced *R. rhodochrous* DAP 96253 Cells Used in the Experiments.

| Media | NHase (units/mg cdw) | Amidase (units/mg cdw) | ACC deaminase (units/mg cdw) |
|---|---|---|---|
| G- | 2 | 0 | 0 |
| G Co | 81 | 0 | 0 |
| G U | 26 | 20 | 5 |
| G Co U | 70 | 4 | 1 |
| G Co U Asn | 60 | 10 | 3 |

(Note:
Activities reported are using the older assay procedure.)

TABLE 5

Monitoring of Fruit Ripening in Control and Catalyst Treated Peaches

| | Initial Measurements | | | After 7 days | | | |
|---|---|---|---|---|---|---|---|
| | Brix after 3 wks at 4° C. | pH | Degree of hardness | Brix | Carbohydrate content (mg/ml) | pH | Degree of hardness/ Comments |
| control | 15.5 | 4 | ++++ | 18 | 167 | 4 | + |
| | | | | | | | ++ |
| G | 15.5 | 4 | ++++ | 16 | 146 | 4 | Several peaches had some degree of discoloration and fungal growth |
| | | | | | | | +++ |
| G Co | 15.5 | 4 | ++++ | 17 | 136 | 4 | Two peaches were slightly wrinkled with a brown spot |
| | | | | | | | +++ |
| G U | 15.5 | 4 | ++++ | 17 | 122 | 4 | One peach showed discoloration with some fungal growth |
| G Co U | 15.5 | 4 | ++++ | 17 | 127 | 4 | +++ |
| G Co U Asn | 15.5 | 4 | ++++ | 17 | 132 | 4 | +++ |

The data shows that *rhodococcal* catalyst was effective in delaying the ripening of fruit after the fruit had been stored in the cold for an extended period. The catalyst was also able to prevent chill injury and fungal growth on the fruit.

The above experiment was repeated several times. In all cases, the catalyst treated peaches showed reduced adverse effects from storage at 4-7° C. Also parallel experiments were conducted where the catalyst was introduced at the time the fruit were place in cold-storage (results were essentially the same as above.)

Example 5: Peaches Subjected to Severe Temperature Transient During Shipping, Then Stored at 6.1° C.

One set of peaches received via air freight apparently experienced a very low temperature transient during shipment. Control peaches showed extremely accelerated decay and mold involvement. Catalyst treated peaches showed reduced adverse effects especially up to 2-weeks at 4-7° C.

TABLE 6

Selected Enzyme Activities from Induced Cells of *R. rhodochrous* DAP 96253.

| NHase (units/mg cdw) | Amidase (units/mg cdw) | Cyanidase | B-cyanoalanine synthetase | ACC deaminase (units/mg cdw) |
|---|---|---|---|---|
| 200 | 27 | 7 | 8 | 26 |

Example 6: Inhibition of *Fusarium* Sporulation by *Rhodococcus rhodochrous* DAP 96253 Through Volatiles

Procedures

Fungal Inhibition

*Rhodococcus rhodochrous* DAP 96253 cultures were started from glycerol stocks stored at −80° C. by transferring 1 ml of the glycerol stock to 250 ml nutrient broth. The culture was incubated at 30° C. while shaking at 150 rpm for 2 days. Nutrient agar plates were inoculated and incubated for 2 days at 30° C.; *Fusarium* sp isolated from peaches was streaked on SAB plates and grown for 7 days. The spores were harvested and diluted to $10^3$ spores/ml.

Compartmentalized Petri dishes (3 or 4 sections per plate) were used in these experiments. Two sections contained YEMEA and the other two sections contained SAB. The YEMEA sections were inoculated with *rhodococcal* cells; the plates were wrapped in parafilm and incubated for a week at 30° C. Following a week of incubation, the *rhodococcal* compartments contained a lawn of bacteria, 50 μl of

*Fusarium* spore suspension was transferred to the SAB sections of the plate. The plates were incubated for three days at 30° C.

*Rhodococcal* cells were also scrapped from YEMEA (8 plates) that contained different supplements such as urea, cobalt chloride, asparagine and suspended in 10 ml phosphate buffer, the cell suspension was transferred to a section in a compartmentalized Petri dish containing no media. A membrane containing *Fusarium* sp spores ($10^3$ spores/ml) was transferred to the section of the plate containing YEMEA media.

Cyanide Production

Cyanide production was assessed using picrate paper method. Picrate paper was prepared by dissolving moist picric acid (1.4 g) in 100 ml of 2.5% sodium carbonate. A Whatman filter paper was immersed in the yellow picrate solution for 20 sec then dried, cut in strips and stored in the dark at −20° C. The yellow strips would turn pink/red in the presence of cyanide.

*Rhodococcus rhodochrous* DAP 96253 was inoculated on YEMEA containing the different supplements (urea, cobalt, asparagine), picrate strips were taped to the lid of the Petri dish, the plates were wrapped in parafilm and incubated for 7 days. *Pseudomonas aeruginosa* (GSU 3) was used as a positive control for cyanide production and to test the hypothesis that cyanide production by bacteria can inhibit *Fusarium* sporulation using compartmentalized plates, GSU 3 was inoculated in one section containing TSA while fungi was inoculated on another section containing SAB.

Results

Figures 19A, 19B, 19C, 19D:
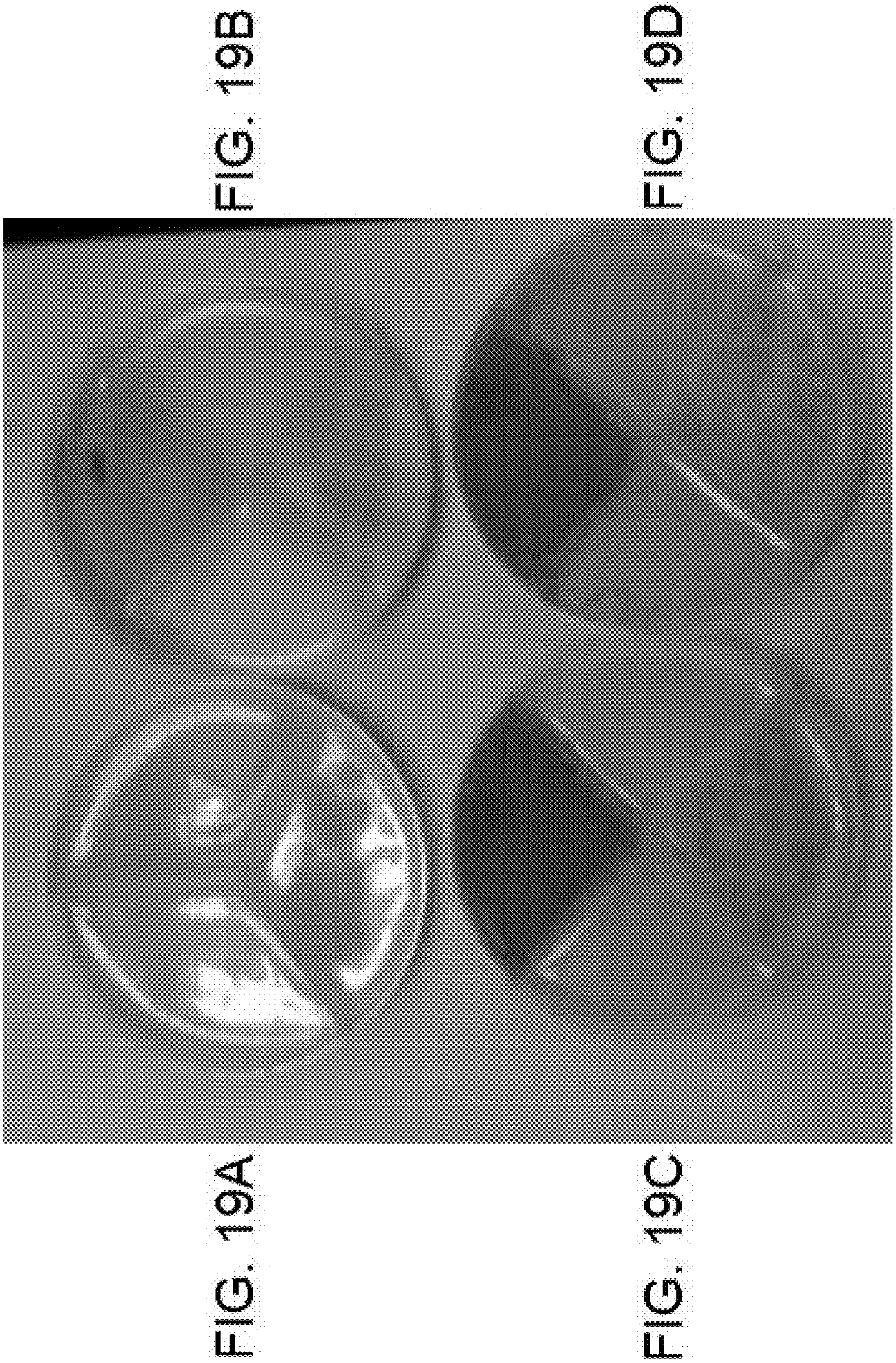
FIGS. 19A to 19D show effect of *Rhodococcal* cells on sporulation of *Fusarium*.
Figures 20A, 20B, 20C, 20D:
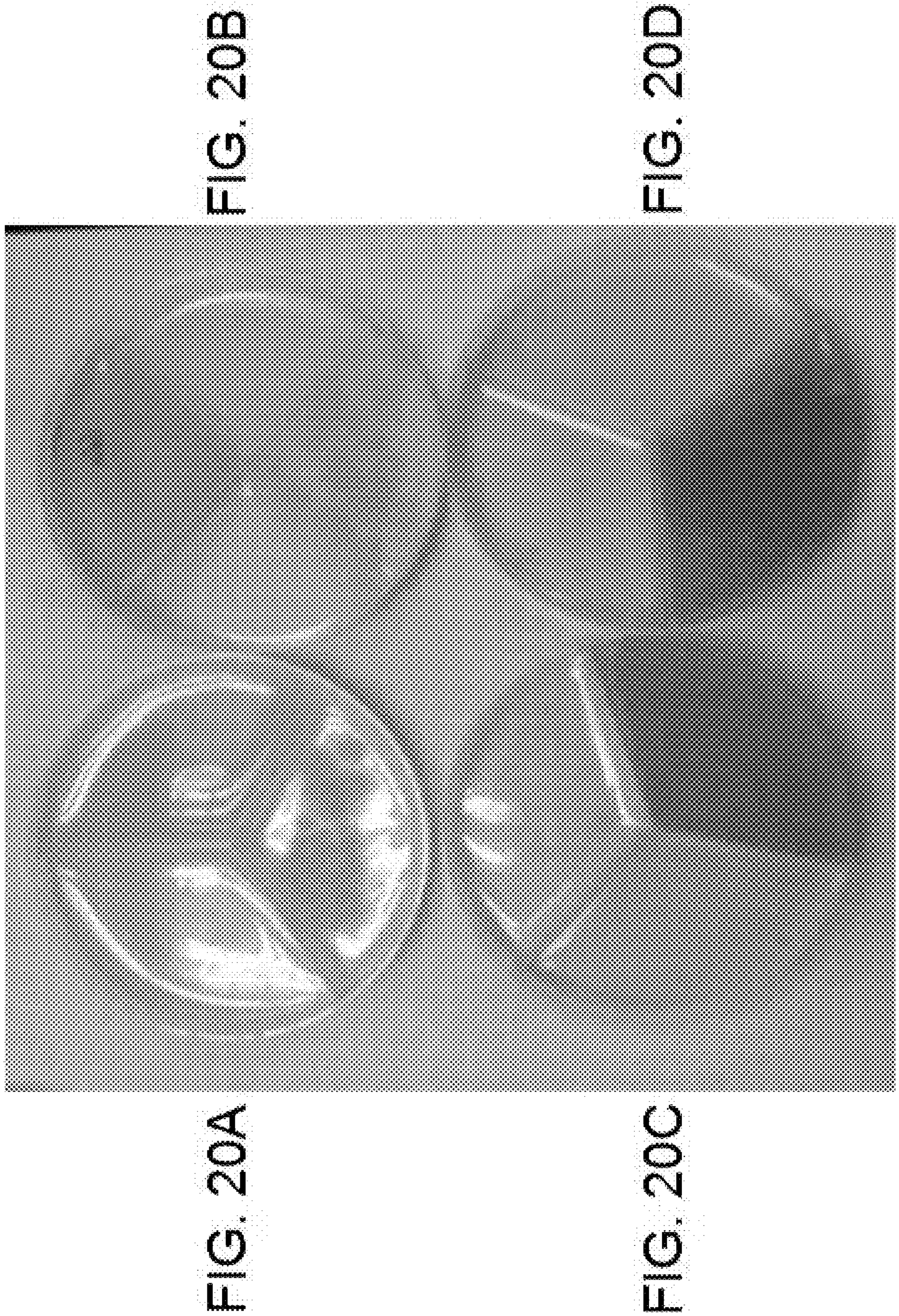
FIGS. 20A to 20D show effect of *Rhodococcal* cells on sporulation of *Fusarium*.
Figures 21A, 21B, 21C, 21D:
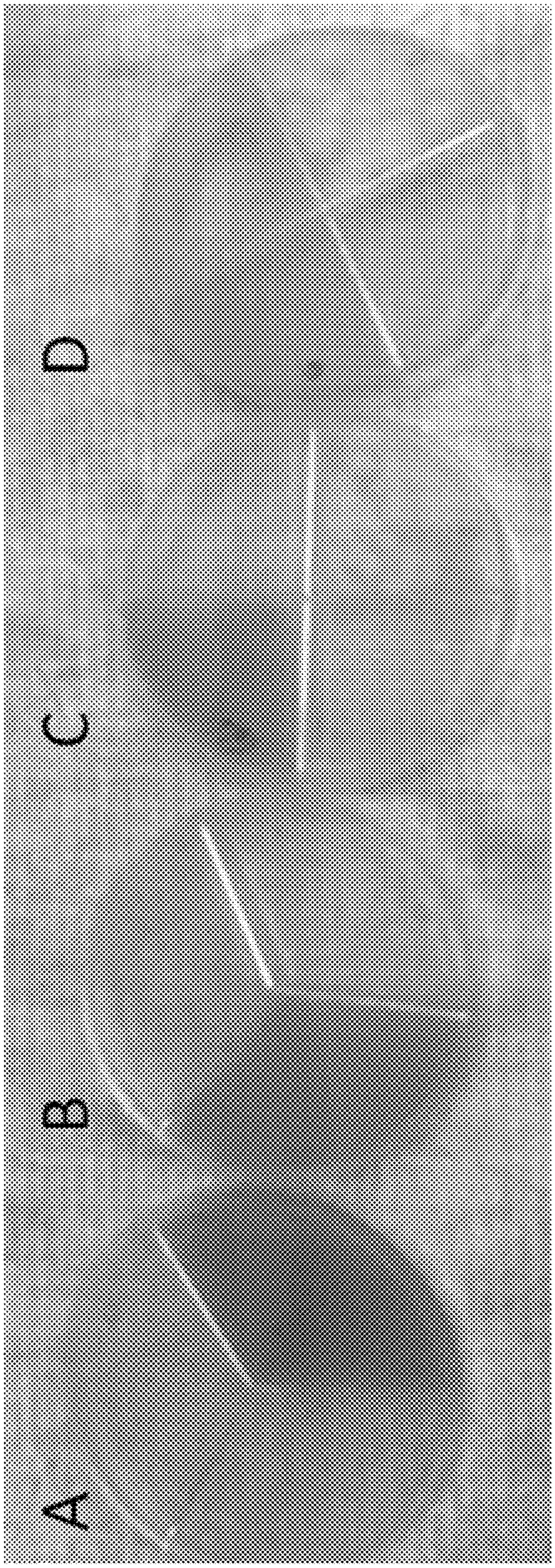
FIG. 21 shows fungal inhibition by *Rhodococcus* after 6 days. *Rhodococcus* was grown on media supplemented with urea (FIG. 21A), cobalt and urea (FIG. 21B), cobalt only (FIG. 21C), or no supplements (FIG. 21D). The same concentration of *Fusarium* spores was inoculated on SAB media in separate compartment on all the plates
Figures 22A, 22B:
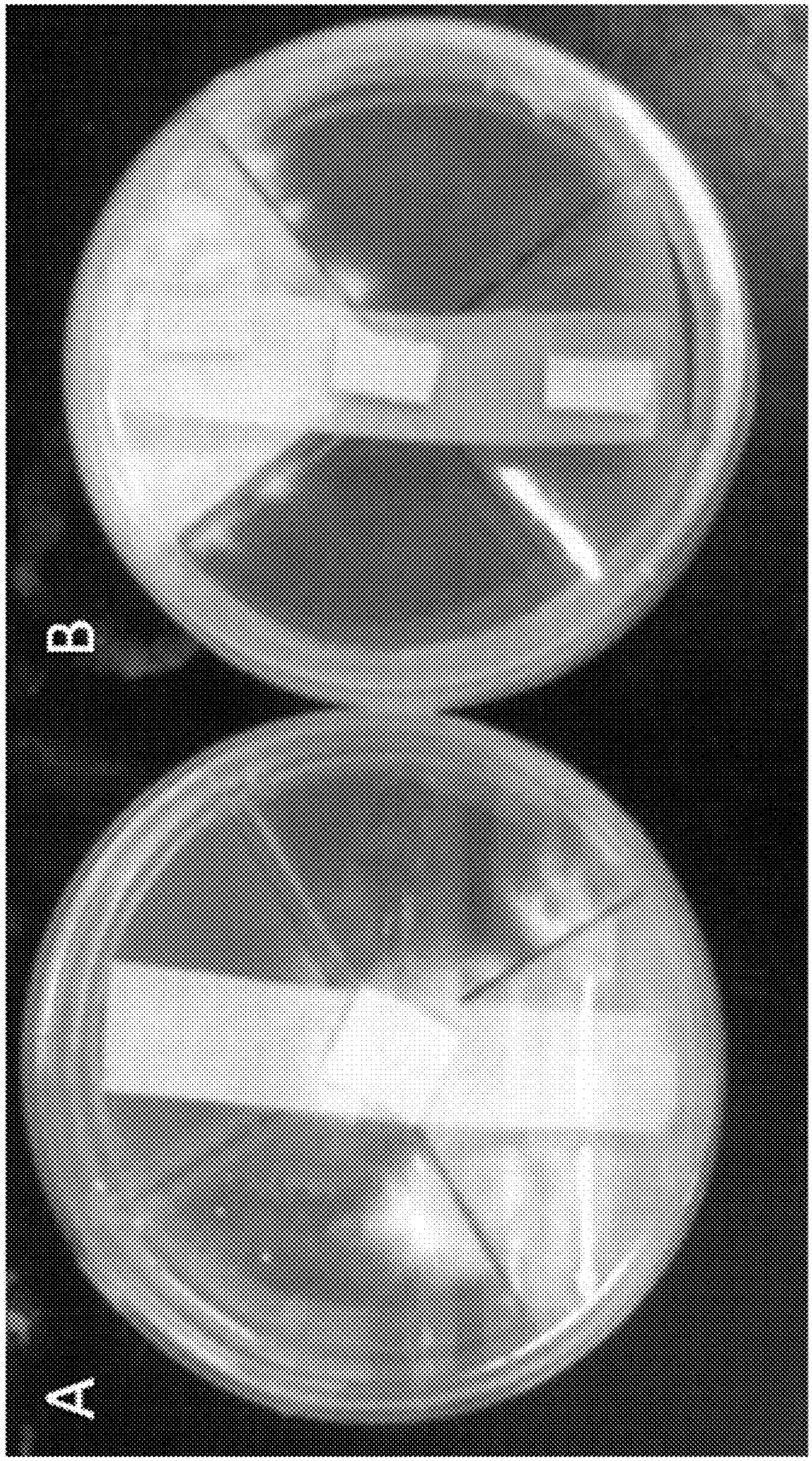
FIG. 22A is a control, with only *Fusarium* inoculated.
FIG. 22B shows *Pseudomonas aeruginosa* (GSU3) inoculated in separate section from *Fusarium*, picrate paper showing positive color change for cyanide production.

*Rhodococcus* was grown on different supplements such as urea, cobalt and asparagine in separate sections from *Fusarium* in a Petri dish. When *Rhodococcus* was grown on media supplemented with urea there was significant inhibition of fungal sporulation/growth (FIG. 20), media without supplementation and media supplemented with cobalt only did not show any delay in fungal sporulation (FIG. 19). FIG. 21 compares *rhodococcal* cells grown without supplements, with urea supplemented, with cobalt supplemented and with cobalt and urea supplementation. FIGS. 19-21 show inhibition while *rhodococcal* cells were growing on media, FIG. 22 shows that cells scrapped from plates supplemented with urea could still be effective in delaying fungal growth. The inhibition observed in these experiments was not due to metabolites or compounds in the media as the fungal and *rhodococcal* growth was separated using compartmentalized plates.

*Rhodococcus rhodochrous* DAP 96253 did not show any cyanide production using the picrate method for detection. *Pseudomonas aeruginosa* GSU 3 showed cyanide production which did not have any effect on the sporulation of *Fusarium* using the same concentration of spores in the *rhodococcal* experiments.

Conclusions

*Rhodococcus rhodochrous* DAP 96253 grown in the presence of *Fusarium* and other fungal species inhibits fungal sporulation. *Rhodococcal* spent media also inhibits/delays fungal sporulation.

These experiments show that the mechanism for fungal inhibition is complex and that it also involves volatiles as the organisms were kept separated using the compartmentalized Petri plates. *Rhodococcal* cells grown in the presence of urea showed significant inhibition of fungal sporulation and growth. This could be due to enzymes induced by urea (ACC deaminase, amidase) metabolizing volatile signals needed by the fungi for sporulation and growth.

It has been shown that cyanide production by bacteria inhibits fungal growth; *rhodococcal* cells did not show any cyanide production using the picrate paper method which suggests that fungal inhibition might be due other volatiles or disruption of volatiles such as ethylene.

What is claimed is:

1. A method for inhibiting or reducing fungal growth in grain, comprising exposing the grain to a composition comprising one or more bacteria, wherein the one or more bacteria are selected from the group consisting of *Rhodococcus rhodochrous* DAP 96253, *Rhodococcus rhodochrous* DAP 96622, *Rhodococcus erythropolis*, and combinations thereof, and wherein the one or more bacteria are provided in a quantity sufficient to inhibit or reduce fungal growth on the grain.

2. The method of claim 1, wherein the one or more bacteria are induced to produce one or more enzymes selected from the group consisting of nitrile hydratases, amidases, asparaginases, ACC deaminases, cyanoalanine synthase-like enzymes, monooxygenases, dioxygenases, cyanidases, and combinations thereof.

3. The method of claim 2, wherein the composition further comprises the one or more enzymes or an enzymatic extract produced by the one or more bacteria.

4. The method of claim 1, wherein the composition further comprises an inducing agent selected from the group consisting of urea, methyl carbamate, methacrylamide, acetamide, cobalt, asparagine or asparagine derivative, and combinations thereof.

5. The method of claim 1, wherein the composition further comprises a stabilizing agent.

6. The method of claim 5, wherein the stabilizing agent is trehalose.

7. The method of claim 1, wherein the one or more bacteria are fixed with glutaraldehyde and cross-linked.

8. The method of claim 1, wherein the one or more bacteria are provided in a coating layer.

9. The method of claim 8, wherein the coating layer is selected from a hydrophobic fatty acid polyester coating or a wax.

10. The method of claim 1, wherein the composition further comprises a magnetic material.

11. The method of claim 8, wherein the magnetic material comprises iron.

12. The method of claim 1, wherein the composition is administered in the proximity of, but not directly on, the grain.

13. The method of claim 1, wherein the composition is administered directly on the grain.

14. The method of claim 1, wherein the grain is in a grain silo.

15. The method claim 1, wherein the grain is selected from the group consisting of a cereal grain, a starchy grain, a grain legume, and an oilseed.

16. The method of claim 15, wherein the cereal grain is selected from the group consisting of maize, sorghum, fonio, millet, rice, rye, barley, oat, triticale, wild rice, and teff.

17. The method of claim 15, wherein the starchy grain is selected from the group consisting of amaranth, quinoa and buckwheat.

18. The method of claim 15, wherein the grain legume is selected from the group consisting of soybean, common bean, chickpea, lima bean, runner bean, pigeon pea, lentil, field pea or garden pea, lupin, mung bean, fava bean, and peanut.

19. The method of claim 15, wherein the oilseed is selected from the group consisting of rapeseed, canola, India mustard, black mustard, sunflower seed, safflower, flax seed hemp seed, and poppyseed.

20. The method of claim 1, wherein the fungal growth is produced by a fungus selected from the group consisting of mold, yeast, mildew, fungi that cause smut, fungi that cause rust, fungi that cause diseases of plants, and fungi that cause diseases of animals.

21. The method of claim 20, wherein the fungus is selected from the group consisting of *Trichoderma* species, *Aspergillus niger, Aspergillus flavus, Aspergillus fumigatis, Alternaria alternata, Epicoccum nigrum, Pichia pastoris, Geomyces destructans, Geomyces asperulatus*, and *Geomyces pannorum.*

22. The method of claim 1, wherein the composition is provided in liquid form.

23. The method of claim 22, wherein the composition further comprises a liquid carrier.

24. The method of claim 23, wherein the liquid carrier is selected from the group consisting of an aromatic hydrocarbon, a substituted naphthalene, a phthalic acid ester, an aliphatic hydrocarbon, an alcohol, and a glycol.

25. The method of claim 1, wherein the composition is provided as a solid and the solid is applied at or near the location.

26. The method of claim 25, wherein the solid further comprises a solid carrier.

27. The method of claim 26, wherein the solid carrier is selected from the group consisting of a dust, a wettable powder, a water dispersible granule, and a mineral filler.

28. The method of claim 27, wherein the mineral filler is selected from the group consisting of calcites, silicas, talcs, kaolins, montmorillonites, attapulgites, and mixtures thereof.

29. The method of claim 1, wherein the composition further comprises one or more exogenous enzymes, wherein the one or more exogenous enzymes are exposed to the grain in a quantity sufficient to inhibit or reduce fungal growth.

30. The method of claim 29, wherein the one or more exogenous enzymes are selected from the group consisting of nitrile hydratase, amidase, asparaginase, ACC deaminase, cyanoalanine synthase-like enzyme, alkane monooxygenase, ammonium monooxygenase, methane monooxygenase, toluene dioxygenase, cyanidase, and combination thereof.

* * * * *